(12) United States Patent
Callaghan

(10) Patent No.: US 11,964,219 B2
(45) Date of Patent: Apr. 23, 2024

(54) SYSTEMS, DEVICES, AND METHODS FOR SYMPHASIC CLOSED-CYCLE HEAT EXCHANGE

(71) Applicant: Scientific 710, LLC, Portland, OR (US)

(72) Inventor: Clancy Callaghan, Hillsboro, OR (US)

(73) Assignee: Scientific 710, LLC, Portland, OR (US)

( * ) Notice: Subject to any disclaimer, the term of this patent is extended or adjusted under 35 U.S.C. 154(b) by 0 days.

(21) Appl. No.: 18/266,606

(22) PCT Filed: Dec. 10, 2021

(86) PCT No.: PCT/US2021/062956
§ 371 (c)(1),
(2) Date: Jun. 12, 2023

(87) PCT Pub. No.: WO2022/125991
PCT Pub. Date: Jun. 16, 2022

(65) Prior Publication Data
US 2024/0033655 A1 Feb. 1, 2024

Related U.S. Application Data

(60) Provisional application No. 63/124,051, filed on Dec. 10, 2020.

(51) Int. Cl.
*B01D 11/02* (2006.01)
*F25B 41/00* (2021.01)

(52) U.S. Cl.
CPC ........ *B01D 11/028* (2013.01); *B01D 11/0207* (2013.01); *B01D 11/0296* (2013.01); *F25B 41/00* (2013.01)

(58) Field of Classification Search
CPC .............. B01D 11/028; B01D 11/0207; B01D 11/0296; B01D 11/0203; B01D 11/0292;
(Continued)

(56) References Cited

U.S. PATENT DOCUMENTS 4,416,119 A 11/1983 Wilson et al.
6,667,015 B1 * 12/2003 Low .................. A23L 27/11
554/12
(Continued)

FOREIGN PATENT DOCUMENTS

CN 207667172 U * 7/2018 .............. B01D 1/00
CN 110064224 A * 4/2019 ............. B01D 11/02
(Continued)

OTHER PUBLICATIONS

English Translation of Yang Patent Publication CN110179667A, Published Aug. 2019. (Year: 2018).*
(Continued)

*Primary Examiner* — Joseph W Drodge
(74) *Attorney, Agent, or Firm* — CALYX LAW; Graham Pechenik; Gregory Dwulet

(57) ABSTRACT

The present invention discloses systems, devices, and methods for symphasic closed-cycle heat exchange, applicable to processes for extraction of compounds from biological materials, such as cannabis and other plants; said systems, devices, and methods incorporating a closed-cycle refrigeration circuit to provide energy savings and other improvements over existing single loop closed-cycle extraction processes.

20 Claims, 4 Drawing Sheets

(58) Field of Classification Search
CPC . A61K 36/185; C11B 1/10; F25B 1/00; F25B 31/00; F25B 41/00; F25B 41/006; F25B 41/20; F25B 41/40
See application file for complete search history.

(56) References Cited

U.S. PATENT DOCUMENTS

| | | | |
|---|---|---|---|
| 9,181,468 | B2 | 11/2015 | Fan et al. |
| 10,208,867 | B2 | 2/2019 | Takada et al. |
| 10,245,525 | B1 * | 4/2019 | Ko ................... B01D 46/0006 |
| 2010/0130762 | A1 * | 5/2010 | Hulse ..................... C11B 1/10 554/21 |
| 2013/0165840 | A1 | 6/2013 | Orge |
| 2017/0312327 | A1 * | 11/2017 | Jones ................ B01D 11/0215 |
| 2019/0143246 | A1 | 5/2019 | Ko |
| 2019/0151771 | A1 * | 5/2019 | Thomas ............... C07D 311/80 |
| 2020/0188812 | A1 | 6/2020 | Galyuk |
| 2020/0199055 | A1 | 6/2020 | Jansen et al. |
| 2020/0346136 | A1 * | 11/2020 | Lantz ..................... B01D 3/40 |
| 2022/0128272 | A1 * | 4/2022 | Lantz ..................... F25B 1/10 |

FOREIGN PATENT DOCUMENTS

| | | | | |
|---|---|---|---|---|
| CN | 110179667 | A * | 8/2019 | ............. F25B 30/02 |
| CN | 114470833 | A * | 5/2022 | |
| RU | 2721704 | C1 * | 5/2020 | ............... C11B 1/10 |

OTHER PUBLICATIONS

English Translation of Dan Patent Publication CN207667172U, Published Jul. 2018. (Year: 2018).*
English Translation of Yang Patent Publication CN11064224A, Published Jul. 2019. (Year: 2019).*
English Translation of Shevtsov Patent Publication RU2721704C1, Published May 2020. (Year: 2020).*
English Translation of Zhu Patent Publication CN 114470833, published May 13, 2022. (Year: 2022).*
Automatic Control Valve Products. Flomatic Valves. (Jul. 21, 2021). Retrieved Nov. 26, 2021, from https://www.flomatic.com/valves/.
Ashlin. What is a capillary tube and why do we need it. Instrumentation and Control Engineering. (Jun. 15, 2020). Retrieved Nov. 26, 2021, https://automationforum.co/what-is-a-capillary-tube-and-why-do-we-need-it/.
Bright Hub Engineering. Capillary tube refrigeration. Capillary tube in refrigeration, Air Conditioning. Bright Hub Engineering. (Dec. 4, 2009) Retrieved Dec. 7, 2021, from https://www.brighthubengineering.com/hvac/58420-capillary-tube-for-refrigeration-and-air-conditioning-systems/.
Butane—thermophysical properties. Engineering ToolBox. (2008). Retrieved Dec. 10, 2021, from https://www.engineeringtoolbox.com/.
Butane extraction: Using blended solvents for the best bho. Professional Extraction Equipment. (Oct. 16, 2016). Retrieved Nov. 14, 2021, from https://precisionextraction.com/2016/10/blended-solvents-butane-propane-extraction/.
BVV. The role of butane/propane in plant extraction. BVV. (Oct. 24, 2018) Retrieved Nov. 14, 2021, from https://shopbvv.com/blogs/bvv-resources/the-role-of-butane-propane-in-plant-extraction.
Cashco. Fluid flow basics of throttling valves. (n.d.). Retrieved Nov. 23, 2021, from https://www.controlglobal.com/assets/Media/MediaManager/RefBook_Cashco_Fluid.pdf.
Cunha, V.M., et al. Carbon dioxide use in high-pressure extraction processes. CO2 Chem., Capture & Oil Recovery. (Aug. 16, 2018):211-240.
Engineering ToolBox. Conductive Heat Transfer. (2003) https://www.engineeringtoolbox.com/conductive-heat-transfer-d_428.html.
How thermostatic expansion valves work. Danfoss. (Dec. 15, 2017). Retrieved Nov. 26, 2021, from https://www.danfoss.com/en-us/service-and-support/case-stories/dcs/how-thermostatic-expansion-valves-work/.
Krawcke, N. A beginning HVAC Tech's Guide for Understanding Superheat. ACHR News RSS. (Apr. 17, 2019). Retrieved Nov. 26, 2021, from https://www.achrnews.com/articles/141034-a-beginning-hvac-techs-guide-for-understanding-superheat.
Neese, B. Three types of heat transfers. Sciencing. (Mar. 13, 2018) Retrieved Dec. 10, 2021, from https://sciencing.com/three-types-heat-transfers-5422262.html.
Nesbitt, B. Handbook of valves and actuators. Elsevier in association with Roles & Associates Ltd. (2007).
Recirculating Chiller F-305 / F-308 / F-314. Recirculating Chiller F-305 / F-308 / F-314 | Buchi.com. (2021). Retrieved Dec. 7, 2021.
Russo, Taming THC: potential cannabis synergy and phytocannabinoid-terpenoid entourage effects. British Journal of Pharmacy. (2011). 163:1344-64.
Stengel, J. Understanding Supercritical Carbon Dioxide (CO2) extraction. Cole. (Nov. 1, 2019). Retrieved Nov. 12, 2021, from https://www.coleparmer.com/tech-article/supercritical-co2-extraction-method.
PCT/US21/62956, International Search Report (ISA/US), Aug. 10, 2022.
PCT/US21/62956, Written Opinion of the International Searching Authority (ISA/US), Aug. 10, 2022.
PCT/US21/62956, International Preliminary Report on Patentability (Chapter I, ISA/US), Jun. 13, 2023.
PCT/US21/62956, PCT Search Strategy and Results (ISA/US), Jul. 22, 2022.

* cited by examiner

SYSTEMS, DEVICES, AND METHODS FOR SYMPHASIC CLOSED-CYCLE HEAT EXCHANGE

CROSS-REFERENCE

This application is a national stage entry under 35 U.S.C. § 371 of PCT/US21/62956, filed Dec. 10, 2021, which claims priority under PCT Article 8(1) and Rule 4.10 to U.S. Provisional Application No. 63/124,051, filed Dec. 10, 2020, both of which are incorporated by reference for all purposes as if fully set forth herein.

TECHNICAL FIELD

Described herein are systems, devices, and methods for symphasic closed-cycle heat exchange, applicable to processes for extraction of compounds from plants and other biological materials.

BACKGROUND OF THE INVENTION

Plants have played an important role in the lives of humans since at least the beginning of recorded history, not only for their use as food, but also as a source of medicine. The medicinal properties of plants are typically the product of natural plant compounds known as phytochemicals.

A. Medicinal Plant Compounds

Generally, phytochemicals are classified into primary and secondary metabolites. Primary metabolites are those that perform an intrinsic physiological function in the plant, for example by being directly involved in normal growth, development, or reproduction. These include chlorophyll, amino acids and proteins, and carbohydrates like cellulose (the main structural component and greatest contributor to the overall biomass of most plants). Primary metabolites generally show no pharmacological actions or effects when taken by humans.

Secondary metabolites are not directly responsible for growth and development but help the plant to survive in its environment. For example, these allow a plant to regulate its metabolic activity, communicate with other organisms (e.g., attract pollinators or deter pathogens), and respond to stress. Secondary metabolites include terpenoids, alkaloids, flavonoids, and phenols. The plant compounds that typically come first to mind as having pharmacological effects in humans—e.g., vitamins, antioxidants, and chemicals like caffeine, nicotine, and morphine—are all secondary metabolites. Numerous secondary metabolites have been shown to have antibacterial, anti-inflammatory, anticancer, antimalarial, antiviral, and other therapeutic effects in humans, and many are used as a drug or were the basis for the design of a drug.

Only in the recent past have scientists been able to isolate and identify the specific secondary metabolites responsible for particular therapeutic effects, and to characterize these compounds chemically. However, it has long been known that plants can be manipulated and treated to separate and extract one or more "active" secondary metabolites of interest from the rest of the plant. When we make a morning cup of tea or coffee, for instance, we are performing the final step in a process that begins with selecting the most caffeine-rich parts of the plant (the tender topmost leaves of the tea plant, or the berries of the coffee tree), preparing these parts for extraction (by curing or roasting), and then using hot water to extract the water soluble compounds (in particular the caffeine) into a brewed beverage to drink. By extracting caffeine in this way—i.e., separating a secondary metabolite from the primary metabolites—we are able to obtain a desired therapeutic effect, without having to ingest or consume the rest of the plant.

B. Medicinal Compounds in Cannabis

One plant that has significant medical potential due to its vast array of secondary metabolites is cannabis. Cannabis is a genus of flowering plants in the family Cannabaceae that is commonly recognized as containing the three species *Cannabis sativa*, *Cannabis indica*, and *Cannabis ruderalis*. Cannabis is believed to be one of the first plants to be cultivated, and has a long history of human use for medicinal purposes. Indeed, in what is considered to be the first pharmacopoeia entry, in 2737 BC, the Chinese Emperor Shen-Nung described cannabis as useful to treat over 100 different ailments. Use of cannabis for medicinal purposes continued across the millennia, as was recorded by the Egyptians, Greeks, Romans, and in many other cultures.

Beginning in the 19$^{th}$ century, however, cannabis use became increasingly vilified, and associated only with its psychoactive and intoxicating effects. This eventually culminated in its illegalization and criminalization in most countries. Although extensive use continued in the shadows, legalization attempts throughout the end of the 20$^{th}$ century repeatedly stalled. To this day, cannabis remains illegal in the United States at the federal level. Nonetheless, two in three Americans support the full legalization of recreational ("adult use") cannabis, and a majority of U.S. states have now legalized cannabis for medical and/or recreational use.

Despite ongoing federal illegality, cannabis today is the most commonly used psychotropic substance in the U.S., after alcohol. Based on recent Gallup polls, 55 million Americans identify as active cannabis users, with nearly 25% of young adults aged 18-25 having consumed cannabis in the prior month, over a third in the past year, and over half at some point in their lives. At present, the U.S. legal cannabis industry employs nearly 250,000 Americans, and is worth an estimated $20 billion, predicted to rise to $100 billion by 2030.

Cannabis plants contain at least 545 distinct compounds across 20 chemical classes, including cannabinoids, terpenes/terpenoids, amino acids, nitrogenous compounds, simple alcohols, aldehydes, ketones, esters, lactones, acids, fatty acids, steroids, non-cannabinoid phenols, pigments, flavonoids, vitamins, proteins, enzymes, glycoproteins, and hydrocarbons.

The secondary metabolites generally associated with the medicinal effects of cannabis are cannabinoids and terpenoids. Over 100 cannabinoids have been isolated from cannabis, including tetrahydrocannabinol (THC), the most widely-known cannabinoid because of its intoxicating effects, resulting in the "high" associated with cannabis use, in addition to moderate analgesic and neuroprotective effects—including a reduction in neuroinflammation and the promotion of neurogenesis. The psychoactive effects of THC are thought to be primarily because of its interaction with $CB_1$ receptors, and mimicry of anandamide—an endogenously-produced neurotransmitter.

$CB_1$ and $CB_2$ (cannabinoid-1 and cannabinoid-2) receptors are part of the endocannabinoid system (ECS) which also includes the CB receptor ligands, 2-AG and AEA, as well as the endocannabinoid synthesizing and degrading enzymes FAAH and MAGL. Other receptors, including but not limited to TRPV1 are closely related to the CB receptors and may explain the allosteric/synergistic effects exhibited, which are a direct result of the various cannabinoids and terpenes found within the cannabis plant. Broadly, the ECS has been implicated in a wide variety of physiological and pathophysiological processes—e.g., neural development, immune function, inflammation, appetite, metabolism and energy homeostasis, cardiovascular function, digestion, bone development and bone density, synaptic plasticity and learning, pain, reproduction, psychiatric disease, psychomotor behavior, memory, wake/sleep cycles, and the regulation of stress and emotional state.

Besides the principle THC isomer, (−)-trans-$\Delta^9$-tetrahydrocannabinol ($\Delta^9$-THC), numerous other double bond and stereoisomers exist, such as $\Delta^8$-THC, the seven-carbon THC homologue $\Delta^9$-trans-tetrahydrocannabiphorol (THCP), and the butyl and heptyl homologues of THC ($\Delta^9$-THCB and $\Delta^9$-THCP, respectively).

Cannabidiol (CBD), another widely-known cannabinoid, does not have intoxicating effects, but has numerous pharmacological properties; it can exert, for example, analgesic, antioxidant, anti-inflammatory, antiemetic, anticonvulsant, antipsychotic, anxiolytic, antidepressant, anticompulsive, antitumoral, neuroprotective, and immunomodulatory effects.

Other naturally-occurring phytocannabinoids in cannabis include, among numerous more, cannabichromene (CBC), cannabigerol (CBG), cannabielsoin (CBE), cannabicyclol (CBL), cannabidinodiol (CBND), cannabicitran (CBT), cannabitriol (CBT), cannabivarin (CBV), cannabigerol monomethyl ether (CBGM), cannabidiphorol (CBDP), tetrahydrocannabiphorol (THCP), and iso-tetrahydrocannabinol (iso-THC).

Terpenoids (or terpenes) are another important secondary metabolite. In cannabis, terpenes are the largest group of phytochemicals, with at least 120 identified molecules. Terpenes are ubiquitous throughout nature, with some estimates concluding that as many as 60 percent of all naturally-produced chemical compounds are members of the class (totaling over 20,000 unique compounds). Although cannabinoids are more popularly understood to be responsible for the mental and physical effects of cannabis, terpenes have demonstrated a variety of such effects as well—with some evidence pointing to a potential "entourage effect," wherein THC and/or CBD interact more effectively with the $CB_1$ and $CB_2$ receptors in the brain, as well as greater efficacy regarding cannabinoid interaction with the endocannabinoid system in the central nervous system (see generally, e.g., Russo, 2011).

As with other plants, consumption of cannabis to get the therapeutic or pharmacologic effect of the active secondary metabolites—e.g., the cannabinoids and terpenes—requires separating them from the rest of the plant. One common way to do this is by simply smoking cannabis itself directly (i.e., smoking cannabis "flower," the dried and cured inflorescences of the female plants). Combustion of cannabis releases the cannabinoids and terpenes from the plant material (among other compounds) into the smoke, which is inhaled into the lungs, allowing cannabinoids (in their decarboxylated form) and terpenes to be absorbed by lung tissue. (The acidic forms of cannabinoids, as they are found in fresh plant material, have some pharmacological properties; generally however, they must be converted into their neutral form through "decarboxylation" by applying heat before they are active and bioavailable in humans.)

Cannabinoids and/or terpenes of interest also may be extracted from the plant material first before being consumed. These cannabis "extracts" can be obtained as liquids, oils, semi-solids, and solids, which can be directly consumed orally and digested, put into forms such as capsules, or added to infused drinks and foods ("edibles"). Cannabis extracts also can be consumed sublingually (i.e., entering the bloodstream under the tongue) in forms such as tinctures and dissolving strips, and they can be applied topically (i.e., absorbed through skin).

Cannabis extracts also can be smoked or vaporized, i.e., ingested via inhalation of marijuana cigarettes (joints), hollowed-out cigars filled with marijuana (blunts), bongs, including those using water; dabs or "dabbing," by using a "dab rig," wherein decarboxylation occurs readily, as with combusting flower; or vaporized liquid inhaled from a pen containing THC cartridges. Because the secondary metabolites are separated from the rest of the plant material, cannabis extracts are of much higher potency than flower, and additionally allow the selection and isolation (and creation or recombination) of particular cannabinoid and/or terpene profiles. Numerous types of extracts and concentrates are known, e.g., wax, shatter, "budder," crumble, live resin, various oils, and others.

C. Extraction of Plant Compounds

"Extraction" in general refers to various processes of obtaining natural phytochemicals from plants. Broadly speaking, the goal of an extraction process is to specifically collect certain sought-after compounds (in this case, the secondary metabolites of interest), while leaving behind any undesirable compounds and residual plant products (i.e., the primary metabolites). Extraction processes vary from the simple (such as preparation of tea or coffee using hot water) to the complex (involving substantial industrial apparatuses and engineering know-how, and multiple controlled parameters).

Extraction processes are common in the cannabis industry. With cannabis extraction, the ultimate goal is typically to obtain the cannabinoids and terpenes while leaving behind undesirable waxes, fats, lipids, and chlorophyll, although extraction processes may be altered to, for instance, obtain a greater percentage of terpenes, etc. Structurally, cannabinoids and terpenes are naturally concentrated in resinous glands called trichomes, which cover the outside of the cannabis plant, but are predominant on the flowers and top leaves. Although one may wish to obtain all or some of the terpenes, or a specific fraction or composition thereof, the term "cannabinoids" is often used herein to refer to the biologically active compounds in a desired extract; however, reference as such is simply used as a shorthand from one exemplary process and, as mentioned, those of ordinary skill will appreciate that extraction procedures using cannabis may be modified to obtain different fractions of cannabinoids, terpenes, and combinations thereof, as well as other cannabis plant compounds; extraction processes using other plant species may be used to obtain other secondary plant metabolites or desired compounds; and extraction processes using other biological materials may be used to obtain other compounds of interest.

Like with obtaining caffeine from tea leaves or coffee beans, extraction of cannabinoids from cannabis is done using a solvent. However, because cannabinoids are lipophilic (i.e., fat-soluble or hydrophobic), water cannot serve as the solvent (caffeine, by contrast, is water-soluble). Instead, typical solvents for cannabis extraction are carbon dioxide, an alcohol, or a hydrocarbon—all lipophilic solvents ("like dissolves like"). Depending on extraction type, this can result in an extract having very high cannabinoid content and purity.

Although extraction is discussed herein by reference to cannabis, it will be readily appreciated that the systems, devices, and methods of the present invention are broadly applicable to extraction of other compounds, non-limiting examples of which include essential oils from other plant material, as well as any other compounds obtained via extraction processes driven by a temperature gradient that cycles solvent useful in breaking down (typically lipophilic) biomaterial throughout a system. Moreover, the disclosed extraction processes also can be used to obtain other compounds of interest from other biological materials, such as animal materials, including animal products, animal byproducts, and animal waste; fungal materials, including from both macroscopic fungi and microscopic fungi—such as *Saccharomyces cerevisiae* or other species of yeast; algae, and bacteria, such as *E. coli*. Further, the disclosed extraction processes are useful to improve those conducted in the oil and gas industry, such as the extraction of hydrocarbon-containing organic matter within coal, oil shale, tar sands and oil sands, crude oil, heavy or extra heavy crude oil, natural gas and petroleum gas, crude bitumen, kerogen, and natural asphalt or asphaltene.

Merely for purposes of elucidating in depth one concrete example, cannabis will be discussed herein; however, the ordinary artisan will readily understand and appreciate the expansive scope of useful applications to which this invention can be directed without undue experimentation or learning outside of the teachings herein and the general knowledge in the art (see, e.g., U.S. Pat. Nos. 2,254,245 and 2,290,209 (cottonseed oil extraction); U.S. Pat. No. 8,092,752 (extraction of oils and fats from oil-bearing substances)).

Different solvents and different extraction methods each have a unique blend of different advantages and drawbacks. Nonetheless, those of ordinary skill are able to balance the tradeoffs and select a solvent and extraction method accordingly, depending on variables to be optimized (e.g., efficiency, cost, characteristics of a desired ultimate product). (Various "solventless" extraction techniques also exist, generally using mechanical principles.)

Broadly, supercritical fluid extraction (SCFE), including carbon dioxide ($CO_2$) extraction, is well-suited for the extraction and purification of compounds possessing a low volatility, and/or those susceptible to thermal degradation, like cannabinoids. The critical point, refers to the maximum thermodynamic state reached by the saturation curve between liquid and vapor phases (Cunha et al., 2018), and is measured by a corresponding critical temperature ($T_c$), and critical pressure ($P_c$). When the substance, in this case $CO_2$, is in the state above the critical temperature and critical pressure, it is referred to as a "supercritical fluid," whereas, when the substance's pressure is above that of its critical point, but below the critical temperature threshold, it is called a "subcritical liquid." $CO_2$'s critical pressure is 73.7 bar (1,068.92 psi), while its critical temperature is 304.15 K (31° C.) (Cunha et al., 2018).

Functionally, carbon dioxide extraction works by first bringing $CO_2$—which is a gas at room temperature and atmospheric pressure—to a "supercritical" state, where it takes on some properties of a liquid and will thus act as a solvent. This is generally done by increasing the temperature and pressure, with pressure being as much as 5,000 psi or higher. The supercritical $CO_2$ is then forced through an extraction vessel packed with ground cannabis material (somewhat like how an espresso machine works), where it breaks the trichomes, allowing dissolution of part of the plant material. A pressure release valve then allows the material to flow into a separate vessel, where an internal compressor and heater are used to adjust pressure and temperature. By fluctuating the temperature, pressure, and flow rate, certain molecules will bind to $CO_2$, allowing separation from the plant. Because $CO_2$ is recyclable, some systems will then reroute $CO_2$ back into the tank to be used during the next batch (Stengel, 2019). Further processing steps may be taken to refine the extract (e.g., dewaxing, winterization, distillation), so it only contains desired compounds. Because of SCFE's usefulness in extraction of more delicate compounds, it is often better suited for terpene preservation, given the relatively low boiling point of most terpenoids.

Supercritical $CO_2$ extraction can have drawbacks. It is a lengthy process, taking roughly four to six hours to extract 20 pounds of plant material, and requires constant observation due to the continuous fluctuations in temperature and pressure. Thus, unless terpenoid preservation is a primary goal of the operation, $CO_2$ extraction may not be well-suited for commercial extraction (Stengel, 2019). Supercritical $CO_2$ extraction techniques are widely known to those of skill (see U.S. Pat. Nos. 10,307,447; 10,092,852; 9,744,200; 9,649,349; 8,895,078; 8,846,409; 6,403,126). Subcritical $CO_2$ extraction techniques also exist, but are generally less efficient (see, e.g., U.S. Pat. No. 10,688,410).

Alcohol extraction works similarly, but with an alcohol used as the solvent (i.e., an organic compound having at least one hydroxyl functional group, — OH, bound to a saturated carbon atom). Primarily, the alcohol used is ethanol, $C_2H_6O$, the purified form (between about 95% to about 100%) of the same ethyl alcohol found in alcoholic spirits. Isopropyl alcohol may be used in producing "hash," made of trichomes processed and removed from the surface of the cannabis plant (Bennett, 2021). Ethanol can be easier to work with than supercritical $CO_2$ because it is a liquid at ordinary temperature and pressure; however, as a polar solvent, it will also readily dissolve water-soluble molecules like chlorophyll.

A variety of ethanol extraction methods are known, including single-stream process that can be conducted under warm or cool conditions, an example of the former being the "Soxhlet technique," which essentially boils ethanol in a flask or pot, then condenses it on a cooled-coil, which then drips through the packed flower material, stripping the cannabinoids and terpenes during the process (June-Wells, 2020). This warm-ethanol technique is generally just a small-batch approach that extracts chlorophyll/waxes and decarboxylates the cannabinoids, and usually requires additional dewaxing and purification steps. Super-cooled extraction, by contrast, extracts fewer waxes and pigments than warm-ethanol extraction, but is much less efficient (June-Wells, 2020). One additional alcohol extraction technique used largely by independent producers is a "tincture," which is made by soaking cannabis in purified ethanol for several weeks—the result being a concentrated solution comprising the active ingredients of cannabis and alcohol. Like $CO_2$ extraction, Ethanol and other alcohol extraction techniques are also widely known in the art (see, e.g., U.S. Pat. Nos. 10,414,709; 10,413,845; 10,406,453; U.S. Pub. Nos. 2017/0333503; 2003/0017216; 2016/0038437).

Hydrocarbon extraction is also performed by passing a solvent through cannabis plant material to obtain the cannabinoids. Here, the solvent is a hydrocarbon (i.e., a molecule that contains only hydrogen and carbon atoms), including any of propane, butane, isobutane, pentane, isopentane, petroleum ether or dimethyl ether, but most commonly propane (CAL), butane ($C_4H_{10}$), or mixtures thereof. One of skill appreciates the different use cases in which hydrocarbon solvents such as propane, butane, mixtures thereof, etc., can be advantageous.

Broadly, propane and butane are both gases at room temperature—the boiling points of propane and butane are −42° C. (−43.6° F.) and −1° C. (30.2° F.) respectively. Given butane's higher boiling point, it can be recondensed in a closed-loop system, negating the need to use extreme temperatures, and enabling passive recovery. Propane, on the other hand, can create significantly more pressure—given its much lower boiling point—which allows for subzero temperatures in the extraction process without the threat of losing pressure. This can be advantageous in that it helps stop the extraction of lipids and waxes, giving a higher purity to the extract. But, unlike butane extraction methods, passive recovery can be difficult through the use of propane alone, requiring a recovery pump to assist with propane recovery.

More generally speaking, hydrocarbons as a whole are nonpolar; thus unlike alcohols they leave behind unwanted chlorophyll. Also unlike alcohols, hydrocarbons used for cannabis extraction are generally a gas at room temperature (as mentioned, the boiling points of propane and butane are −42° C. and −1° C. respectively). As hydrocarbon chains get longer, boiling points increase; for example, the boiling points of pentane ($C_5H_{12}$), hexane ($C_6H_{14}$), and heptane ($C_7H_{16}$), are 36° C., 68.72° C., and 98.44° C. respectively.

Like $CO_2$ and alcohol extraction methods, hydrocarbon extraction is generally understood by those of ordinary skill in the art. The main steps of a hydrocarbon extraction begin with the solvent as a chilled liquid, and terminate with it being converted to a heated gas. In early hydrocarbon extraction methods, solvents were often purged or lost as vapor to the atmosphere in the final step—making the process expensive to perform (by requiring repeated replacement of new solvent) as well as dangerous (as flammable solvents sometimes caused explosions, resulting in injuries and property damage). Newer, "closed-cycle" extraction methods allow the process to be performed more safely, and conserve solvent by recovering and recycling the evaporated hydrocarbon from the collection tank back to the solvent storage tank to be used again. In these methods, the collection tank and the solvent storage tank are connected by a return channel, so the entire circuit is sealed (see, e.g., U.S. Pat. Nos. 9,144,751; 9,145,532; 9,587,203; 9,682,333; 9,789,147; 9,926,512; 10,329,513; U.S. Pub. Nos. 2017/0113161; 2019/0374873.)

Various means exist to recover the used solvent from the collection tank. In "passive" methods, the thermal gradient between the chilled solvent tank and the heated collection tank alone drives the return. As it is heated into a gaseous state, the solvent expands, which creates pressure in the collection tank that forces the gaseous solvent through the solvent return channel. The return channel terminates in the chilled solvent reservoir where the gaseous solvent is chilled so that it condenses back into a liquid. The condensation of the gaseous solvent reduces the volume of the solvent and thus generates a partial negative pressure which further draws gaseous solvent from the collection reservoir. The condensed solvent may then be recirculated through the equipment, or stored for use in later extraction cycles.

In "active" methods, a vacuum pump may be used to draw solvent through the cycle by creating a negative pressure differential in the line that pulls solvent through the line. A refrigerant recovery pump also may be used to draw vapor from the collection tank back to the solvent storage tank through the return channel, by pulling the solvent directly through the pump itself, and helping to compress the gaseous solvent vapor back into liquid phase. In other methods pressure from an inert gas like nitrogen may assist flow of or drive the solvent.

Such prior systems may permit hydrocarbon solvent to be recirculated and recycled, reducing waste and risk. However, closed-cycle hydrocarbon extraction processes require enormous inputs of energy to chill the solvent tank and heat the collection tank, increasing expense and environmental impact. Although different means exist in the art to perform the chilling and heating required, such means contribute appreciably to the energy consumption and expense of extraction. There is therefore a need to develop inventive methods of cannabis extraction and processing equipment that lessens the environmental impact of cannabis production, while maximizing ease of use and efficiency.

Applicant herein discloses novel systems, devices, and methods that substantially increase the efficiency of extraction methods, reduce the energy input required, and in many ways as will become apparent below, provide significant improvements over the current art.

INCORPORATION BY REFERENCE

Each patent, publication, and non-patent literature cited in the application or in the section entitled References is hereby incorporated by reference in its entirety as if each was incorporated by reference individually. Unless specifically stated otherwise, reference to any document herein is not to be construed as an admission that the document referred to or any underlying information in the document is prior art in any jurisdiction, or forms part of the common general knowledge in the art.

BRIEF SUMMARY OF THE INVENTION

The present invention discloses systems, devices, and methods for symphasic closed-cycle heat exchange, applicable to processes for extraction of compounds from biological materials, such as cannabis and other plant materials. Such systems, devices, and methods have numerous significant advantages over the prior art, as further discussed herein.

"Symphasic" refers to the use of a closed-cycle device or system, namely a refrigeration system (or "refrigeration circuit"), running alongside and parallel to a solvent extraction device or system and arranged so as to run in synchrony therewith, forming together a single device or system (e.g., a symphasic closed-cycle extraction system) for extraction of compounds from biological material (and/or non-biological material), such as in some embodiments one comprising: (1) a sealable closed-cycle solvent extraction circuit; and (2) a sealable closed-cycle refrigeration circuit.

In some embodiments, "symphasic" also refers to a sealable closed-cycle refrigeration circuit when used as a device, i.e., a closed-cycle heat exchange device, together with (or capable of being used together with) a solvent extraction device or system, and in particular one comprising a closed-cycle solvent extraction circuit, to create together a symphasic closed-cycle extraction system.

Broadly, "symphasic" is derived from "sym-," from the Greek sun meaning "together" or "with" (as in "sympathy" and "synchrony"); and "—phasic" meaning "of or pertaining to a phase," wherein "phase" has the meanings both from chemistry ("a distinct and homogeneous form of matter, i.e. a solid, liquid, or gas") and from physics ("the relationship between successive states or cycles of an oscillating or repeating system"). The full meaning of "symphasic" will be readily understood following a review of Applicant's disclosure and claims, and an appreciation of their scope and spirit.

In brief summary are the following aspects and embodiments of the invention.

In some embodiments are systems for extraction of compounds from biological material, the systems comprising: a sealable closed-cycle solvent extraction circuit comprising: a solvent tank, structured to hold an extraction solvent; a material column, structured to hold a biological material for extraction; a collection tank, structured to receive an extraction solution; and a return channel, structured to provide fluid communication between the collection tank and the solvent tank; and a sealable closed-cycle refrigeration circuit comprising: an evaporator, thermally coupled to the solvent tank; a compressor; a condenser, thermally coupled to the collection tank; and a control means.

In some embodiments are systems for extraction of compounds from biological material, the system comprising: a sealable closed-cycle solvent extraction circuit comprising: a solvent tank, structured to hold an extraction solvent; a material column, structured to hold a biological material for extraction; a collection vessel, structured to receive an extraction solution; an evaporation vessel, fluidly coupled to the collection vessel; and a return channel, structured to provide fluid communication between the evaporation vessel and the solvent tank; and a sealable closed-cycle refrigeration circuit comprising: an evaporator, thermally coupled to the solvent tank; a compressor; a condenser, thermally coupled to the evaporation vessel; and a control means.

In some embodiments, the refrigeration circuit is capable of creating a thermal gradient to drive solvent within the extraction circuit (although such thermal gradient need not be the only means by which solvent circulates within the extraction circuit, and therefore one of skill will understand "a thermal gradient to drive solvent" as meaning a thermal gradient may contribute some or provide all of the means by which the solvent circulates within the extraction circuit).

In some embodiments, the thermal gradient to drive the extraction solvent is created by a transfer of heat from the condenser to the collection tank and a transfer of heat from the solvent tank to the evaporator.

In some embodiments, the refrigeration circuit is capable of creating a thermal gradient to drive solvent within the extraction circuit.

In some embodiments, the thermal gradient to drive solvent is created by a transfer of heat from the condenser to the evaporator vessel and a transfer of heat from the solvent tank to the evaporator.

In some embodiments, the thermal gradient drives solvent within the extraction circuit, so that a biological compound concentrate is obtained from the biological material for extraction.

In some embodiments, the biological material for extraction is a plant material, and the biological compound concentrate is a plant compound concentrate.

In some embodiments, the plant material is a cannabis material, and the plant compound concentrate is a cannabis concentrate.

In some embodiments, the cannabis concentrate comprises one or more cannabinoids, and optionally one or more terpenes.

In some embodiments are systems for extraction of compounds from biological material, the system comprising: a sealable closed-cycle solvent extraction circuit comprising: a solvent tank, structured to hold an extraction solvent; a material column, structured to hold a biological material for extraction; a collection tank, structured to receive an extraction solution; and a return channel, structured to provide fluid communication between the collection tank and the solvent tank; and a sealable closed-cycle refrigeration circuit comprising: an evaporator, thermally coupled to the solvent tank; a compressor; a condenser, thermally coupled to the collection tank; and a throttling device.

In some embodiments are systems for extraction of compounds from biological material, the system comprising: a sealable closed-cycle solvent extraction circuit comprising: a solvent tank, structured to hold an extraction solvent; a material column, structured to hold a biological material for extraction; a collection vessel, structured to receive an extraction solution; an evaporation vessel, fluidly coupled to the collection vessel; and a return channel, structured to provide fluid communication between the evaporation vessel and the solvent tank; and a sealable closed-cycle refrigeration circuit comprising: an evaporator, thermally coupled to the solvent tank; a compressor; a condenser, thermally coupled to the evaporation vessel; and a throttling device; wherein the refrigeration circuit is capable of creating a thermal gradient to drive solvent within the extraction circuit.

In some embodiments, the refrigeration circuit is capable of creating a thermal gradient to drive solvent within the extraction circuit (although such thermal gradient need not be the only means by which solvent circulates within the extraction circuit, and therefore one of skill will understand "a thermal gradient to drive solvent" as meaning a thermal gradient may contribute some or provide all of the means by which the solvent circulates within the extraction circuit).

In some embodiments, the thermal gradient to drive the extraction solvent is created by a transfer of heat from the condenser to the collection tank and a transfer of heat from the solvent tank to the evaporator.

In some embodiments, the refrigeration circuit is capable of creating a thermal gradient to drive solvent within the extraction circuit.

In some embodiments, the thermal gradient to drive solvent is created by a transfer of heat from the condenser to the evaporator vessel and a transfer of heat from the solvent tank to the evaporator.

In some embodiments, the thermal gradient drives solvent within the extraction circuit, so that a biological compound concentrate is obtained from the biological material for extraction.

In some embodiments, the biological material for extraction is a plant material, and the biological compound concentrate is a plant compound concentrate.

In some embodiments, the plant material is a cannabis material, and the plant compound concentrate is a cannabis concentrate.

In some embodiments, the cannabis concentrate comprises one or more cannabinoids, and optionally one or more terpenes.

In some embodiments are closed-cycle heat exchange devices for use with a solvent extraction system for extraction of compounds from biological material, the device comprising: an evaporator; a compressor; a condenser; and a control means.

In some embodiments, the device is capable of creating a thermal gradient to drive a solvent in the solvent extraction system when the device is thermally coupled thereto.

In some embodiments, the evaporator is thermally coupled to a solvent tank of the solvent extraction system, and the condenser is thermally coupled to a collection tank of the solvent extraction system.

In some embodiments, the evaporator is thermally coupled to a solvent tank of the solvent extraction system, and the condenser is thermally coupled to an evaporator vessel of the solvent extraction system.

In some embodiments, the thermal gradient to drive solvent is created by a transfer of heat from the condenser to the collection tank and a transfer of heat from the solvent tank to the evaporator.

In some embodiments, the thermal gradient to drive solvent is created by a transfer of heat from the condenser to the evaporator vessel and a transfer of heat from the solvent tank to the evaporator.

In some embodiments, the thermal gradient drives solvent within the solvent extraction system, so that a biological compound concentrate is obtained from the biological material for extraction.

In some embodiments, the biological material for extraction is a plant material, and the biological compound concentrate is a plant compound concentrate.

In some embodiments, the plant material is a cannabis material, and the plant compound concentrate is a cannabis concentrate.

In some embodiments, the cannabis concentrate comprises one or more cannabinoids, and optionally one or more terpenes.

In some embodiments are closed-cycle heat exchange devices for use with a solvent extraction system for extraction of compounds from biological material, the device comprising: an evaporator; a compressor; a condenser; and a throttling device.

In some embodiments, the device is capable of creating a thermal gradient to drive a solvent in the solvent extraction system when the device is thermally coupled thereto.

In some embodiments, the evaporator is thermally coupled to a solvent tank of the solvent extraction system, and the condenser is thermally coupled to a collection tank of the solvent extraction system.

In some embodiments, the evaporator is thermally coupled to a solvent tank of the solvent extraction system, and the condenser is thermally coupled to an evaporator vessel of the solvent extraction system.

In some embodiments, the thermal gradient to drive solvent is created by a transfer of heat from the condenser to the collection tank and a transfer of heat from the solvent tank to the evaporator.

In some embodiments, the thermal gradient to drive solvent is created by a transfer of heat from the condenser to the evaporator vessel and a transfer of heat from the solvent tank to the evaporator.

In some embodiments, the thermal gradient drives solvent within the solvent extraction system, so that a biological compound concentrate is obtained from the biological material for extraction.

In some embodiments, the biological material for extraction is a plant material, and the biological compound concentrate is a plant compound concentrate.

In some embodiments, the plant material is a cannabis material, and the plant compound concentrate is a cannabis concentrate.

In some embodiments, the cannabis concentrate comprises one or more cannabinoids, and optionally one or more terpenes.

In some embodiments are methods of extracting compounds from biological material in a solvent extraction system, the method comprising: packing a biological material for extraction into a material column; passing a liquid solvent from a solvent tank through the material column; collecting a solution of the liquid solvent and biological compounds in a collection tank; recovering a gaseous solvent by evaporating the liquid solvent; recondensing the gaseous solvent as a recovered liquid solvent in the solvent tank; and obtaining a biological compound concentrate containing the biological compounds; wherein a heat exchange device is used to evaporate the liquid solvent and to recondense the gaseous solvent, the heat exchange device comprising a closed-cycle refrigeration circuit, thermally coupled to the solvent extraction system.

In some embodiments, the heat exchange device comprises: an evaporator, capable of recondensing the gaseous solvent; a compressor; a condenser, capable of evaporating the liquid solvent; and a control means.

In some embodiments, the heat exchange device is capable of creating a thermal gradient to drive a solvent in the solvent extraction system when the device is thermally coupled thereto.

In some embodiments, the heat exchange device comprises: an evaporator, capable of recondensing the gaseous solvent; a compressor; a condenser, capable of evaporating the liquid solvent; and a throttling device.

In some embodiments, the heat exchange device is capable of creating a thermal gradient to drive a solvent in the solvent extraction system when the device is thermally coupled thereto.

In some embodiments, the biological material for extraction is a plant material, and the biological compound concentrate is a plant compound concentrate.

In some embodiments are methods of using a thermal gradient to drive a solvent within a solvent extraction system, the method comprising: evaporating the solvent using a condenser, when the solvent is in liquid form; recondensing the solvent using an evaporator, when the solvent is in gaseous form; wherein the condenser and the evaporator are fluidly connected as part of a heat exchange device thermally coupled to the solvent extraction system.

In some embodiments, the plant material is a cannabis material, and the plant compound concentrate is a cannabis concentrate.

In some embodiments, the cannabis concentrate comprises one or more cannabinoids, and optionally one or more terpenes.

These and other objects, features, improvements, and advantages of the present invention may be more clearly understood and appreciated from a review of the following detailed description of the disclosed embodiments and examples, and by reference to the appended claims. The foregoing summary has been made with the understanding that it is to be considered as a brief and general synopsis of only some of the objects and embodiments disclosed herein, is provided solely for the benefit and convenience of the reader, and is not intended to limit in any manner the scope, or range of equivalents, to which the appended claims are lawfully entitled.

BRIEF SUMMARY OF THE DRAWINGS

To further clarify various aspects of the present invention, a more particular description of the invention will be rendered by reference to certain exemplary embodiments thereof which are illustrated in the included figures. It should be understood and appreciated that the figures depict only illustrated embodiments of the invention and are therefore not to be considered limiting of its scope. As such, where the figures included herein are illustrated diagrammatically, and without any specific scale, they are simply provided as qualitative illustrations of the concepts of the present invention, and not intended to limit the invention to any particular dimensions, proportions, configurations, or orientations. The relative placement of individual pieces (above, below, left, right), and the relative direction of flow (clockwise, counterclockwise), are also merely figurative.

Different configurations and orientations of the pieces together are contemplated, and individual pieces may be replaced or removed, as suitable, and the sizes, shapes, materials, colors, textures, and other features and characteristics of the pieces may be added to, subtracted from, or altered without changing the overall purpose and effect of the invention.

Figure 1:
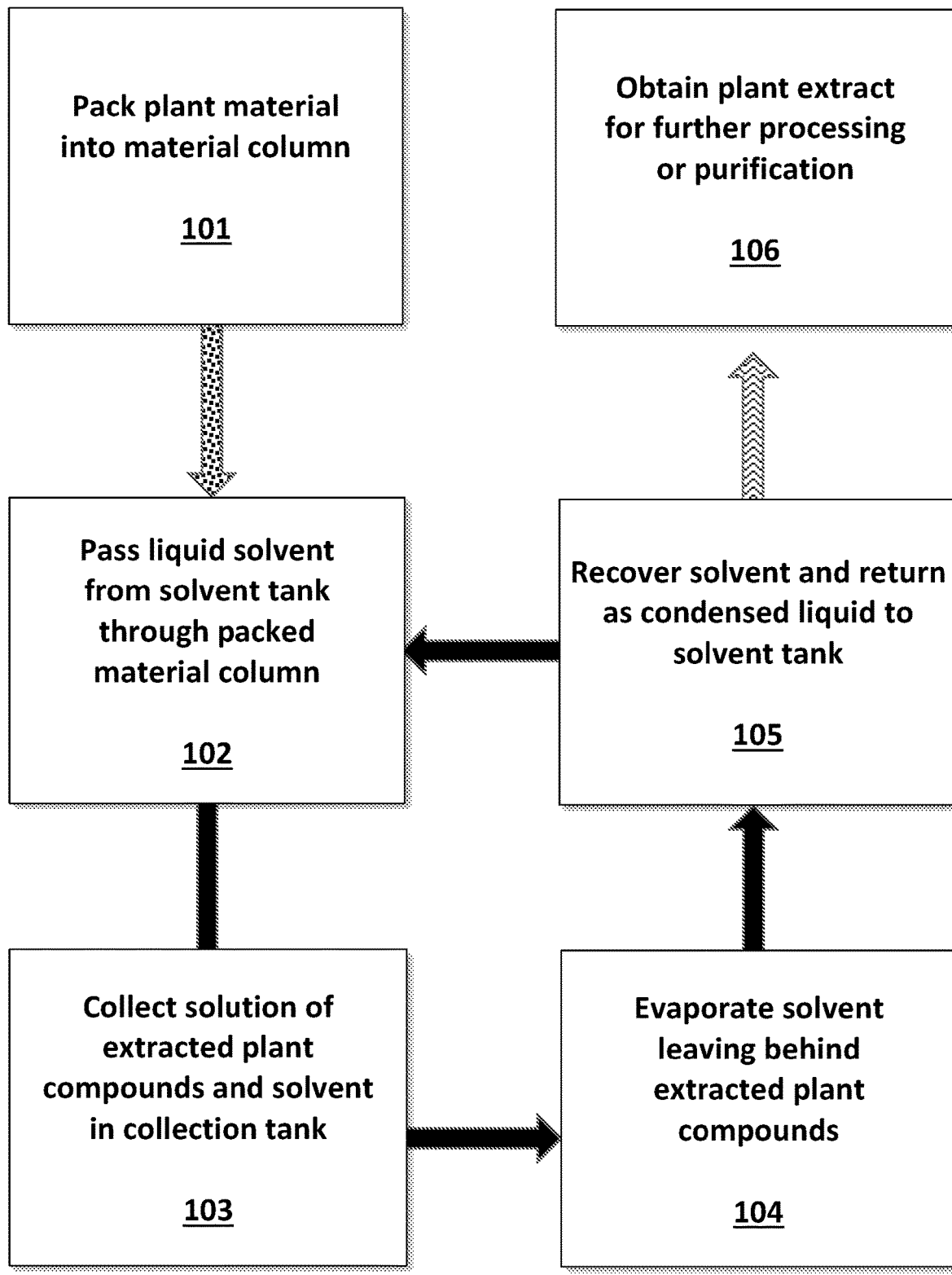

Certain aspects of the invention are further described and explained with additional specificity and detail, but still by way of example, by reference to the accompanying figures:

FIG. 1 shows a flow chart of an exemplary standard closed cycle extraction system.

Figure 2:
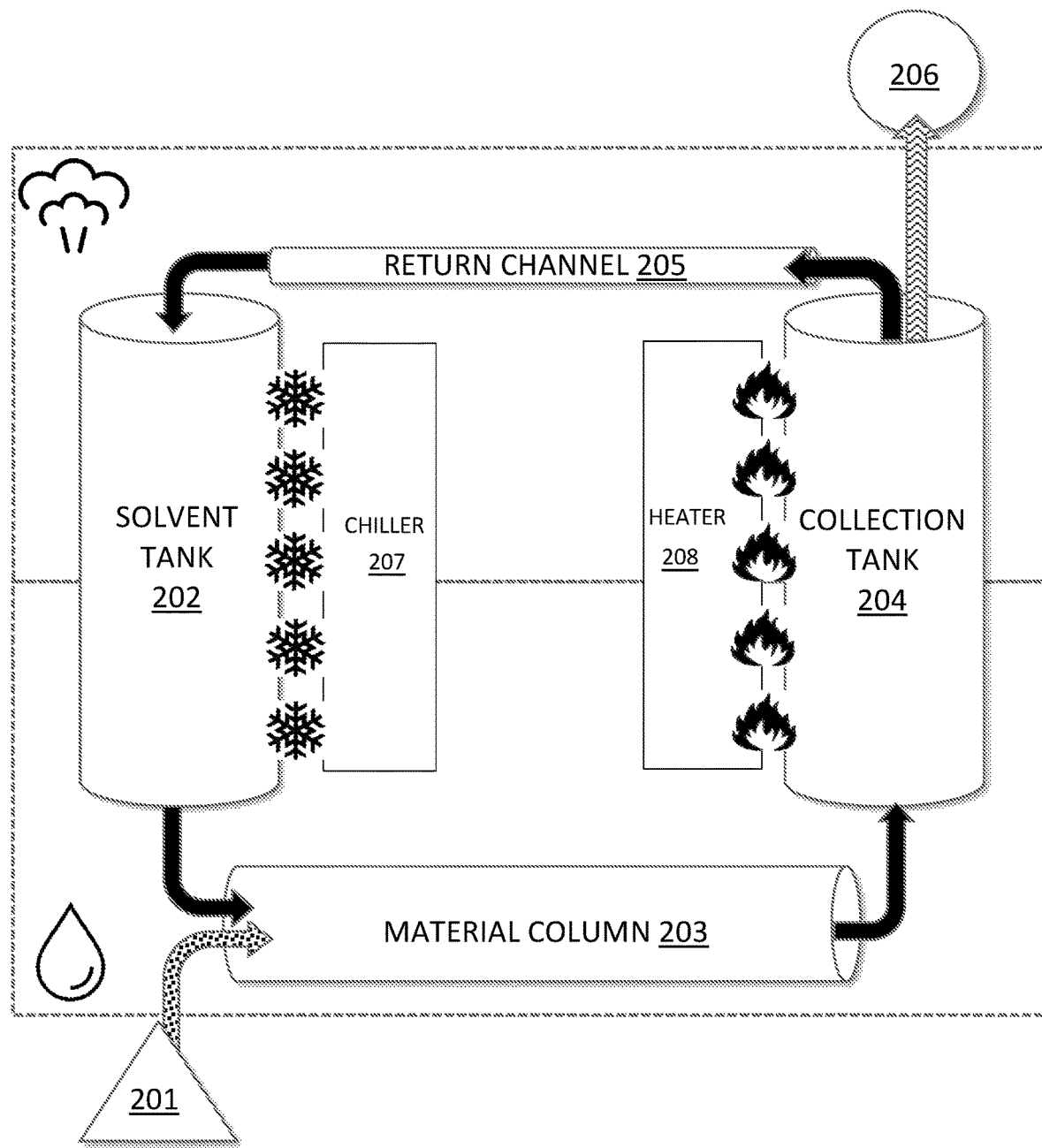

FIG. 2 shows a diagrammatic representation of an exemplary standard closed-cycle extraction system, which uses a chiller and heater.

Figure 3:
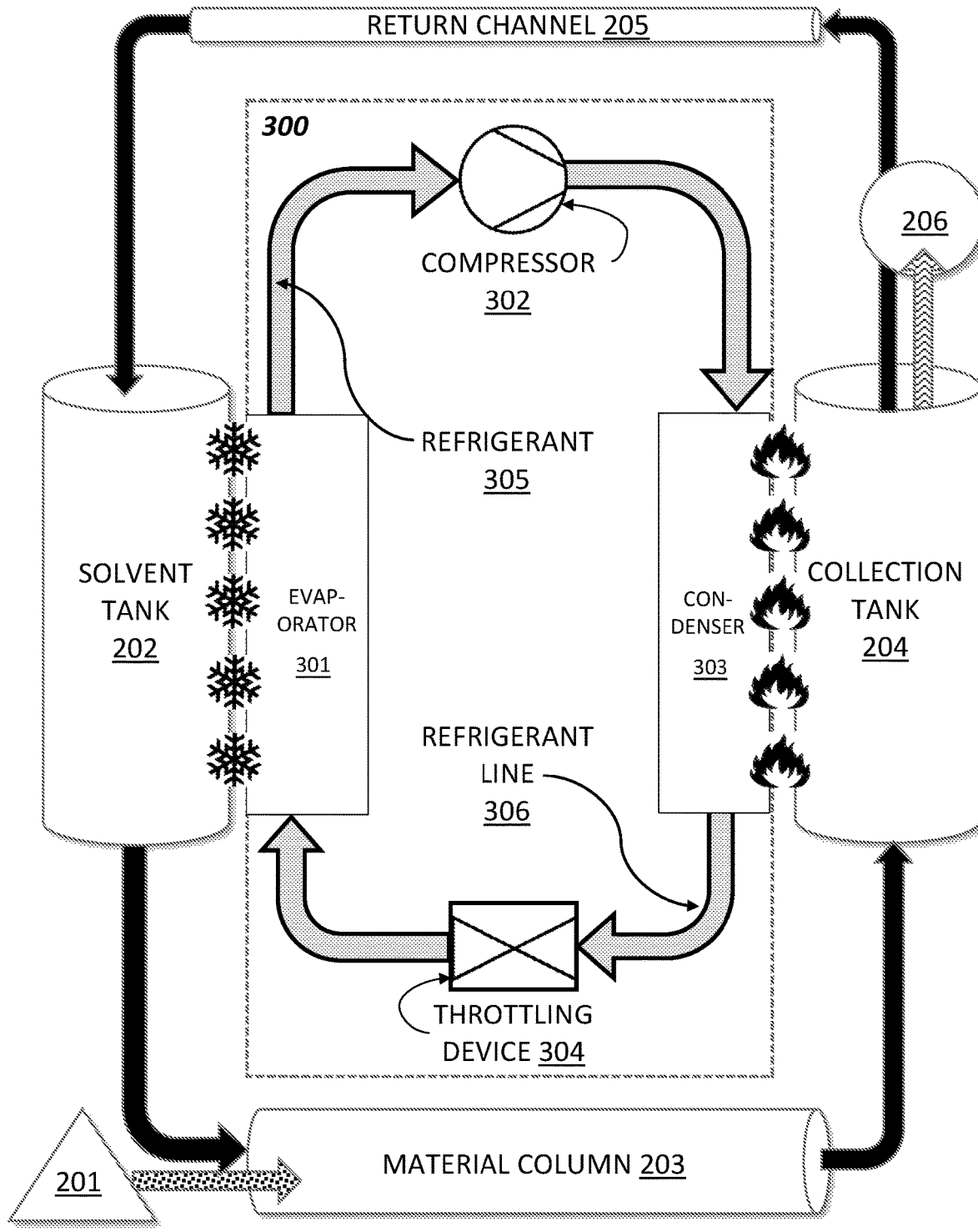

FIG. 3 shows a diagrammatic representation of an exemplary symphasic closed-cycle extraction system, according to one embodiment of the invention, comprising a sealable closed-cycle solvent extraction circuit and a sealable closed-cycle refrigeration circuit.

Figure 4:
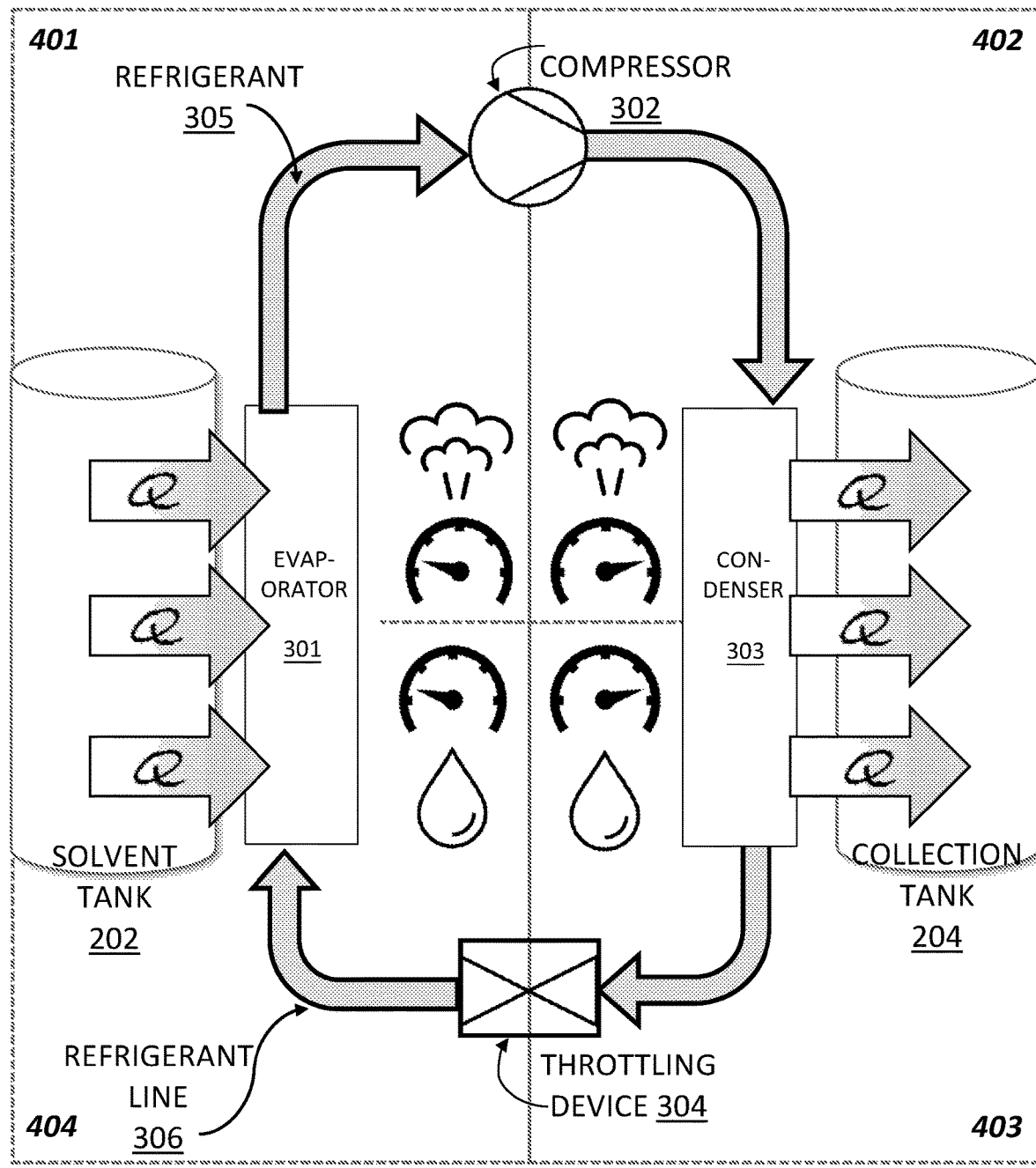

FIG. 4 shows a diagrammatic representation of an exemplary symphasic closed-cycle extraction system, according to one embodiment of the invention, thus also showing use of a closed-cycle heat exchange device, while highlighting, figuratively, the exchange of heat between the refrigeration circuit and certain components of the solvent extraction circuit (and the resultant pressures and phases of matter)—but without showing all components thereof.

DETAILED DESCRIPTION OF THE INVENTION

Among the various aspects of the invention are systems, devices, and methods for symphasic closed-cycle heat exchange, applicable to processes for extraction of compounds from biological materials, such as cannabis and other plant materials, as well as fungal materials and animal materials, including animal products and byproducts, and animal waste.

While the invention is now further described in terms of particular embodiments, examples, and applications, and by reference to the exemplary embodiments that are depicted in the accompanying figures, this description it is not intended to in any way limit its scope to any such embodiments, examples, and applications, and it will be understood that many modifications, substitutions, alternatives, changes, and variations in the described embodiments, examples, applications, and other details of the invention illustrated herein can be made by those skilled in the art without departing from the spirit of the invention, or the scope of the invention as described in the appended claims, including all equivalents to which they are lawfully entitled.

For example, although reference will be made herein to "plant materials," "plant matter," "plant extracts," "plant compounds," and the like, it will be readily understood and appreciated that the systems, devices, and methods of the invention are not applicable only to cannabis and other plants, but will be used to advantage in the extraction of other biological materials from fungal, animal, and other sources as well (e.g., algae and bacteria). And indeed, one of skill will recognize the applications in extraction of non-biological materials as well, including but not limited to hydrocarbon extraction useful in the oil and gas industry, such as extraction of hydrocarbon-containing organic matter within coal, oil shale, tar sands and oil sands, crude oil, heavy or extra heavy crude oil, natural gas and petroleum gas, crude bitumen, kerogen, natural asphalt and/or asphaltene. Reference to plants, and to cannabis in particular, in both the background of the invention and the description of the invention itself, is simply to help orient the reader and the skilled artisan to one exemplary use.

Various modifications, as well as a variety of other uses in different applications, also will be readily apparent to those skilled in the art, and the general principles defined herein may be applied to a wide range of aspects. Thus, the invention is not intended to be limited to the aspects presented, but is to be accorded the widest scope consistent with the principles and novel features disclosed herein. The description below is designed to make such embodiments apparent to a person of ordinary skill in the art, in that the embodiments shall be both readily cognizable and readily creatable without undue experimentation, solely using the teachings herein together with the general knowledge of the art.

The terminology used herein is for describing particular embodiments and is not intended to be limiting. When introducing elements of the present invention or the embodiments thereof, the articles "a," "an," "the," and "said" are intended to mean that there are one or more of the elements. Any reference to an element in the singular is therefore not intended to mean "one and only one" unless specifically so stated, but rather "one or more"; therefore, the term "or" standing alone, unless context demands otherwise, shall mean the same as "and/or." The terms "comprising," "including," "such as," and "having" are also intended to be inclusive and not exclusive (i.e., there may be other elements in addition to the recited elements). Thus, for example, the terms "including," "may include," and "include," as used herein mean, and are used interchangeably with, the phrase "including but not limited to." The word "exemplary" is used herein to mean "serving as an example, instance, or illustration." Any aspect, embodiment, process, or implementation described herein as "exemplary" is therefore not to be construed as necessarily preferred or advantageous over others. Unless defined otherwise, all technical or specialized terms herein have the meaning as commonly understood by one of ordinary skill in the art to which this invention belongs.

Among these various aspects and embodiments of the invention are systems, devices, and methods for symphasic closed-cycle heat exchange, applicable to processes for extraction. This disclosure is not limited to particular embodiments described, as such may vary. For example, while butane is described as being the liquid solvent in some of the exemplary systems, devices, and methods herein, it will be readily understood and appreciated that the systems, devices, and methods of the invention may be used with other solvents, including other hydrocarbon and alcohol solvents, such as propane, hexane, ethanol, methanol, and the like, as well as mixtures thereof, and in a variety of combinations and proportions, with only such modifications and variations as would be understood by those of ordinary skill based on the teachings herein in view of the general knowledge of the art, such as modifications in temperatures, pressures, and/or pressure gradients.

Because it is the process most commonly used, for purposes herein, "hydrocarbon" extraction will refer to extraction by hydrocarbons that are gases at room temperature (e.g., propane and butane), unless context clearly indicates otherwise. It will be appreciated that "blended" solvents also can be used for hydrocarbon extraction (e.g., a mix of 30% propane and 70% butane, or commonly a 50/50 or 70/30 mix thereof, or values in between, as well as any mix from about 1/99 to about 99/1, as would be appreciated by one of skill), and the choice of blend will affect the parameters of the process and the end product, just as does the choice of solvent itself (e.g., the temperature and pressure that should be used, the length of time solvent should be in contact with plant material, the plant compounds that are obtained), in ways also understood to those of skill. To speak broadly of some examples, but without being bound by theory, a 70% butane/30% propane blend can be useful in producing shatter and budder-based extracts, the former having a substantially brittle texture with low tensile strength, while the latter has a texture similar to that of butter, as the propane/butane mixture allows for the extraction of a fuller terpene profile, lighter color, and lower viscosity than using butane alone. Likewise, 100% propane may be used for specialty products like high-terpene extractions or sugar consistency extract products. That said, terpenes can be caustic and volatile, and at too high a concentration they may irritate an end user's throat and prevent enjoyable consumption. Such variables will be within the ken of those of skill.

In simple outline, cannabis hydrocarbon extraction works by: (1) taking a hydrocarbon solvent, substantially chilled so as to be in a liquid state, from a solvent storage tank; (2) running the liquid hydrocarbon solvent through a material column packed with cannabis plant material (which may or may not be milled or ground to increase surface area), wherein the liquid hydrocarbon solvent passes over the material and dissolves the cannabinoids, forming a cannabinoid-rich solution; (3) collecting the cannabinoid-rich solution in a collection tank; and (4) heating the collected contents in the collection vessel, or as received subsequently, in an evaporation vessel to above the boiling point of the solvent—so the solvent volatizes—leaving behind a concentrated cannabinoid extract substantially devoid of the solvent. In subsequent steps, the resulting cannabinoid crude extract can be further processed, refined, and/or purified.

Although any systems, devices, and methods similar or equivalent to those described herein can be used in the practice of the invention, certain exemplary systems, devices, and methods are now described.

To provide a fuller appreciation of the claimed invention, reference is made to the Figures. FIG. 1 shows a flow chart of an exemplary closed cycle extraction system. In this exemplary closed cycle extraction system, plant matter sought to be extracted is first packed within a material column at step 101. Second, a solvent, such as a hydrocarbon liquid solvent like propane, butane, isobutane, pentane, isopentane, petroleum ether, methyl tert-butyl ether, diethyl ether, or any mixture thereof, is then passed from a storage tank through the packed material column at step 102. Third, the solution of the extracted plant compounds in the solvent flow into and are collected in a collection tank at step 103. Fourth, the solvent is evaporated (via means known to those of skill, including but not limited to ambient evaporation, rotary evaporation, and use of a vacuum oven) from the plant extract solution at step 104. Fifth, the solvent is recovered and recycled back to the storage tank, where it is condensed back as a liquid at step 105, and returns to 102. Last, at step 106, the crude plant extract is obtained, which may be further processed, refined, or purified, if so desired.

It will be appreciated from FIG. 1 that plant material ready for extraction enters at 101 and crude plant extract ready for further processing exits at 106; solvent continuously cycles through the process from 102 to 103, 104, and 105, from where it returns back to 102.

Thus, while the diagram shows, for illustrative purposes, solvent present in various specific locations within the system, solvent may be present in certain other specific locations or in all locations at any given time when the system is operational, and those of skill will appreciate where solvent is located at a particular point in running operation. Although reference is made to this exemplary system, in other embodiments, plant extract may be winterized or dewaxed or otherwise further processed before the solvent is evaporated and recovered. Such techniques, which will be known to those of skill, can clarify crude extract having higher concentrations of undesirables, and increase the potency of the final product. They can involve cooling the solvent solution with dissolved solute extracts for a given amount of time until waxes and other constituents (which are physically and chemically different from the oil and are currently considered undesirable) begin to form a precipitate within the solution so they may be filtered out. For example, one can add cold ethanol to the primary extract or store the primary extract at a temperature of between about −29° C. to about −60° C. for about 48 hours to form a characteristic "waxy" precipitate, and then remove the precipitate via filtration. "Filtration" may refer to any physical separation process useful for removing impurities or unwanted particles based on the size of the impurities or particles via a device having a pore size large enough to allow desired contents to freely pass, but small enough to prevent the unwanted impurities or particles from doing the same. One exemplary means of filtration is through the utilization of activated carbon. In some embodiments herein, a product therefore may be winterized, dewaxed, and/or filtered.

Additionally, in some embodiments, the method may also include decarboxylation prior to extraction. Herein, decarboxylation refers to the process of removing the extra carboxyl ring/group attached to the cannabinoid chain. Generally, decarboxylation of cannabis plant material is a product of temperature, pressure, and time. At standard pressure, decarboxylation will begin to occur after being exposed to temperatures of at least about 104° C. for between about 30 minutes to about 45 minutes. However, when exposed to a vacuum, decarboxylation may begin to occur at temperatures as low as about 70° C. Thus, in embodiments wherein decarboxylation prior to extraction is desired, the cannabis plant material should be exposed to temperatures in excess of 104° C., such as about 104° C., about 105° C., about 106° C., about 107° C. about 108° C., about 109° C., about 110° C., about 111° C., about 112° C., about 113° C., about 114° C., about 115° C., about 116° C., about 117° C., about 118° C., about 119° C., about 12.0° C., about 121° C., about 122° C., about 12.3° C., about 124° C., about 125° C., about 126° C. about 127° C., about 128° C., about 129° C., about 130° C., about 131° C., about 132° C., about 133° C., about 134° C., about 135° C., about 136° C. about 137° C., about 1.38° C., about 139° C., about 140° C., about 141° C., about 1.42° C., about 143° C., about 144° C., about 145° C., about 146° C., about 147° C., about 148° C., about 149° C., about 150° C., temperatures greater than 150° C., such as 175° C., 200° C., or 225° C., or values in between, as would be apparent to one of skill; for between about 30 to about 45 minutes, including about 30 minutes, about 31 minutes, about 32 minutes, about 33 minutes, about 34 minutes, about 35 minutes, about 36 minutes, about 37 minutes, about 38 minutes, abort 39 minutes, about 40 minutes, about 41 minutes, about 42 minutes, about 43 minutes, about 44 minutes, about 45 minutes; and more than about 45 minutes, including but not limited to about 50 minutes, about 60 minutes, about 75 minutes, about 90 minutes, about 120 minutes, and values in between, or longer in other embodiments and at other temperatures, as would be apparent to one of skill, and depending on atmospheric pressure.

In some embodiments, cannabis plant material is "fresh frozen" prior to extraction. Generally, in such embodiments, the cannabis plant material (typically, freshly harvested material) is frozen at a temperature of between about 0° C. to about −100° C. In some embodiments, the cannabis plant material is frozen at a temperature of between about 20° C., to about −100° C. In some embodiments, the cannabis plant material is frozen at a temperature of between about −50° C., to about −90° C. In some embodiments, the cannabis plant material is frozen at a temperature of about 0° C., about −1° C., about −2° C., about −3° C., about −4° C., about −5° C., about −6° C., about −7° C., about −8° C., about −9° C., about −10° C., about −11° C., about −12° C., about −13° C., about −14° C., about −15° C., about −16° C., about −17° C., about −18° C., about −19° C., about −20° C., about −21° C., about −22° C., about −23° C., about −24° C., about −25° C., about −26° C., about −27° C., about −28° C., about −29° C., about −30° C., about −31° C., about −32° C., about −33° C., about −34° C., about −35° C., about −36° C., about −37° C., about −38° C., about −39° C., about −40° C., about −41° C., about −42° C., about −43° C., about −44° C., about −45° C., about −46° C., about −47° C., about −48° C., about −49° C., about −50° C., about −51° C., about −52° C., about −53° C., about −54° C., about −55° C., about −56° C., about −57° C., about −58° C., about −59° C., about −60° C., about −61° C., about −62° C., about −63° C., about −64° C., about −65° C., about −66° C., about −67° C., about −68° C., about −69° C., about −70° C., about −71° C., about −72° C., about −73° C., about −74° C., about −75° C., about −76° C., about −77° C., about −78° C., about −79° C., about −80° C., about −81° C., about −82° C., about −83° C., about −84° C., about −85° C., about −86° C., about −87° C., about −88° C., about −89° C., about −90° C., about −91° C., about −92° C., about −93° C., about −94° C., about −95° C., about −96° C., about −97° C., about −98° C., about −99° C., about −100° C., and values in between, and at any such temperatures as would be appreciated by one of skill, for at least about 36 hours, including at least about 40 hours, at least about 44 hours, at least about 48 hours, at least about 56 hours, at least about 64 hours, at least about 72 hours, at least about 96 hours and, in some embodiments, the cannabis plant material may be frozen at the above-referenced temperatures for greater than about 96 hours.

In some embodiments, the cannabis plant material is not fresh frozen prior to extraction. In some embodiments, the cannabis plant material is freshly harvested cannabis. In some embodiments, the cannabis plant material is dried and cured prior to extraction. As with cannabis plant material, other non-cannabis plant material can be extracted after being freshly harvested, after being fresh frozen, and/or after being dried and cured, including any combination(s) thereof.

In some embodiments, the cannabis is sourced from a single seed source, or tissue culture, e.g., with a particular cannabinoid and/or terpene profile chosen for a specific end result. In some embodiments, the cannabis is sourced from a single strain of cannabis. In some embodiments, the cannabis is sourced from more than one cannabis strain, including at least 2, at least 3, at least 4, at least 5, at least 6, at least 7, at least 8, at least 9, at least 10, or, in some embodiments, the cannabis strain may be sourced from more than 10 separate cannabis strains.

In some embodiments, the cannabis strain or cannabis strains selected may be selected due to the specific qualities of the cannabis, including a cannabis strain naturally possessing high concentrations of THC (measured by dry weight %), a cannabis strain naturally possessing low concentrations of THC (measured by dry weight %), or a cannabis strain possessing any specific proportion or combination of cannabinoids, terpenoids, flavonoids, etc., as would be appreciated by one of skill.

In some embodiments, a practitioner may choose a cannabis strain useful in producing industrial hemp. In such embodiments, strains possessing high concentrations of CBDA/CBD, and substantially low concentrations of THC/THCA are preferred. Per the USDA, "industrial hemp" consists of any part of the plant species *Cannabis sativa* L., whether growing or not, containing a Δ-9 tetrahydrocannabinol (THC) concentration of no more than three-tenths of one percent (0.3%) on a dry weight basis, measured as total THC by the Colorado Department of Agriculture (CDA) via the post-decarboxylation process (2021). Herein, "low" and "high" may also be relative terms, wherein "low" refers to concentrations below that of a material possessing "high" concentrations, while "high" concentrations necessarily refer to materials possessing concentrations greater than those possessing "low" concentrations.

In some embodiments, the strain or strains of cannabis used in the extraction method of the invention is/are chosen to selectively "affect" various cannabinoid receptors in any of the nervous system, immune system, or other various tissues/organ systems. "Affect," as it relates to the invention's effects on various cannabinoid receptors, includes psychoactive, therapeutic, prophylactic, and analgesic effects caused by cannabinoid "agents;" wherein "agent" is broadly defined as a compound that "modulates" (inhibits or activates) the activity of a cannabinoid receptor (i.e., $CB_1$ or $CB_2$).

In some embodiments, the strain or strains of cannabis used in the extraction method of the invention may be chosen from all forms of cannabis plant material, including but not limited to *Cannabis sativa*, *Cannabis indica*, *Cannabis ruderalis*, and including all subspecies, varieties, cultivars, and chemovars thereof. In some embodiments, the extraction process of the invention may be used to obtain a cannabis extract with an extraction profile comprising any combination of medically viable compounds therein, including cannabinoids, cannabinoid acids, nitrogenous compounds, amino acids, proteins, enzymes, glycoproteins, hydrocarbons, simple alcohols, aldehydes, ketones, fatty acids, simple esters and lactones, steroids, terpenes, non-cannabinoid phenols, flavonoids, vitamins, and pigments.

FIG. 2 shows a diagrammatic representation of an exemplary closed cycle extraction system, such as could be used in the process outlined in FIG. 1. This exemplary extraction system of FIG. 2 includes a solvent tank 202, a material column 203, a collection tank 204, and a return channel 205. In some embodiments, the return channel is configured to provide fluid communication between the collection tank and the solvent tank. Herein, "fluid communication," "fluidly coupled," or "in fluid communication" refers to a structure configured to allow fluid to flow between two or more objects. Thus, herein, the return channel should be construed to include a means of providing fluid flow between two or more objects, non-limiting examples of which include at least one pipe constructed of a substantially-solid material possessing an interior diameter large enough to allow the material within to flow between the two or more objects, thereby establishing fluid communication with the same, wherein the two or more objects are, in this case, the collection tank and solvent tank. Note, however, such a means is merely illustrative, and other means of providing fluid flow between two or more objects, which would be immediately apparent to one of skill, are within the spirit of the invention as disclosed herein.

It will also be readily appreciated that components in fluid communication typically will be necessarily in fluid communication during operation of the device or system (i.e., as a solvent extraction process is occurring), but may be (and often, need to be) separated or detached or otherwise brought apart from such fluid communication for other uses, e.g., to load plant material into the material column, to load solvent or top up additional solvent into the solvent tank, to remove the collection tank, collection vessel, and/or evaporation vessel to obtain plant compound concentrate for further processing, and the like, as understood by those of skill.

In some embodiments, additional components will be connected either in line or in parallel (as between any two or more objects disclosed herein), and thus reference to a return channel between a collection tank and a solvent tank (or any other reference to a component between two or more objects) will be immediately appreciated as not excluding other configurations involving one or more other components, such as in this instance involving a return channel, a collection tank, a solvent tank, and at least one or more other components either in line or in parallel. Additionally, in some embodiments, any one or more components may be combined into a single physical object, such that, for example, the return channel and collection tank may be a single physical object, the return channel and solvent tank may be a single physical object, or the return channel, collection tank, and solvent tank may all together be a single physical object, and the separation of pieces, components, objects, and the like, for purposes of description, is merely for conceptual clarity and ease of linguistic reference, and is not intended to be limiting of the actual physical design.

To begin, plant matter to be extracted 201 is first packed into the material column 203, corresponding to step 101 (which may, or may not, be milled or ground so as to optimize surface area, and is typically tightly-packed; methods of packing a column vary, but will be understood by those of general skill). Solvent from solvent tank 202, herein termed "extraction solvent" or "extract solvent" is then passed through the packed material column 203 (step 102) (of course, one of skill will readily appreciate that the components may be separated to load plant material, and then be brought into fluid communication to allow solvent to flow in between, and sealed together by a variety of known means).

The plant compounds of interest (e.g., soluble secondary metabolites such as cannabinoids and/or terpenes) are dissolved into the solvent (it will be readily appreciated that other compounds may be dissolved as well, although the extraction process may be designed to minimize and/or eliminate unwanted dissolved plant material as described herein), and this solution (the "extraction solution") flows into collection tank 204 (step 103). Then the solvent (generally, at least a substantial portion thereof) is evaporated from collection tank 204 (step 104) and returned through return channel 205 back to solvent tank 202 (step 105), from where the process can begin again (steps 101, 102). The plant compound concentrate (i.e., crude plant extract) 206 is obtained (step 106), for example by separating or opening the collection tank to remove it, using known methods, and may undergo further processing, such as further removal of solvent, refinement, or purification—as would be appreciated by one of skill—to yield a final plant extract according to operator goals.

Optionally, a vacuum pump and/or refrigerant recovery pump may be used in the return channel 205 to aid recovery. Herein, "vacuum pump" refers to a device capable of removing gas molecules from a sealed volume to leave behind a partial vacuum (Fritz, 2013). Vacuum pumps are common in the art and known to those of skill; exemplary devices include, but are not limited to, positive displacement pumps, such as rotary vane pumps, diaphragm pumps, liquid ring pumps, piston pumps, scroll pumps, screw pumps, wankel pumps, external vane pumps, booster pumps, multistage roots, toepler pumps, and lobe pumps; momentum transfer pumps, including both diffusion and turbomolecular pumps; regenerative pumps, entrapment pumps, and venturi vacuum pumps.

A vacuum pump also may be used to draw solvent from solvent tank 202, or elsewhere, to create a negative pressure differential to draw solvent along the line. Herein, "negative pressure" refers to a state wherein the pressure of the system (or portion of the system) affected by the vacuum pump is less than the pressure of the surrounding system (or other portions of the system) (Angstrom-Tech-Admin, 2016). For example, a vacuum pump may be used to lower the pressure in the solvent tank relative to the pressure ahead of the solvent tank down the line, toward where the solvent is desired to flow (i.e., wherein the negative pressure differential therefore draws solvent away from the solvent tank, and in the desired direction). In some embodiments, the negative pressure differential (i.e., the difference in pressure between the area affected by the vacuum pump and the surrounding system) is between about 1 kPa to about 350 kPa. In some embodiments, the negative pressure differential created by the vacuum pump is between about 75 kPa and about 275 kPa. In some embodiments, the negative pressure differential created by the vacuum pump is about 10 kPa, about 20 kPa, about 30 kPa, about 40 kPa, about 50 kPa, about 60 kPa, about 70 kPa, about 80 kPa about 90 kPa, about 100 kPa, about 110 kPa, about 120 kPa, about 130 kPa, about 140 kPa, about 150 kPa, about 160 kPa, about 170 kPa, about 180 kPa, about 190 kPa, about 200 kPa, about 210 kPa, about 220 kPa, about 230 kPa, about 240 kPa, about 250 kPa, about 260 kPa, about 270 kPa, about 280 kPa, about 290 kPa, about 300 kPa, about 310 kPa, about 320 kPa, about 330 kPa, about 340 kPa, about 350 kPa, and values in between, as would be apparent to one of skill. In some embodiments, the negative pressure differential created by the vacuum pump is less than about 10 kPa, including about 9 kPa, about 8 kPa, about 7 kPa, about 6 kPa, about 5 kPa, about 4 kPa, about 3 kPa, about 2 kPa, about 1 kPa, and values in between, as would be appreciated by one of skill. In some embodiments, the negative pressure differential created by the vacuum pump is greater than about 350 kPa, including about 400 kPa, about 500 kPa, about 750 kPa, about 1,000 kPa and, in some embodiments, is greater than about 1,000 kPa. Negative pressure differentials as well as temperatures and pressures for different solvents and mixtures thereof will be readily apparent to those of skill using the teachings herein and the general knowledge in the art.

Depending on the parameters and/or desired end result, and within the skill of those in the art, other inline components may be added, including additional vessel(s) before or after collection tank 204 (such as a winterization and/or dewaxing vessel), a filter along the return channel 205 (such as a desiccant filter), and an inert gas supply (such as for nitrogen gas, which has a lower density than butane and can be used to assist in driving solvent through the system). Other components, which may be added at various points of the process to various devices, can include temperature and pressure gauges, regulators, sight glasses and view ports, vents, valves, drains, inlets, clamps and connectors, controllers, and the like, as would be known to those of skill. It will be readily appreciated that the invention described herein can be used with extraction systems regardless of the presence or absence of such additional components; particular build specifications and requirements will vary according to the teachings herein combined with known design choices and the general knowledge in the art.

Critical to certain implementations of the process shown in FIG. 2 are chiller 207 and heater 208. It will be understood from general knowledge and the description herein that the solvent is a liquid during part of the process, and a gas during the other part. The dashed boundaries of FIG. 2 indicate that the solvent is a gas in the top portion of the diagram, and a liquid in the bottom diagram; however, it will be understood that the phase change is gradual and the delineation in the figure is suggestive only. Meaning, where the solvent is indicated (by graphical representation in the top left and bottom right corners) as a "gas" on the top portion of the diagram, it may, in some embodiments, be mostly composed of gas, with residual liquid, while where it is indicated as a "liquid," it may, in some embodiments, necessarily be mostly a liquid with residual gas. The phase changes of the solvent play a central role in driving the extraction process by creating a thermal gradient or "heat engine."

Herein, a "thermal gradient," "temperature gradient," "thermal engine," or "heat engine" refers to the sum of a change in temperature over a given distance. Broadly, and without being bound by theory, as the differential between the first temperature and the second temperature increases, and the distance between the same decreases, the ensuing "gradient" also increases. As particles are affected by temperature—heat causes an increase in an atom's motion, which also increases its kinetic energy and causes the substance to expand, decreasing its density (while an absence of heat, or a decrease in thermal energy does the opposite, causing a substance to constrict, increasing its density)—a thermal gradient can also be understood to include a pressure differential caused by unequal heating across a given distance. This difference in pressure (the result of a temperature gradient), causes a substance to move from an area of higher pressure to an area of lower pressure. The greater the pressure differential (or thermal gradient), the greater the force applied to the system which, necessarily, but without being bound by theory, increases the flow-rate of the material.

As measured by kPa, in some embodiments, as will be discussed herein, the thermal gradient created by the phase-changing solvent has a pressure differential of between about 1 kPa to about 1,000 kPa. In some embodiments, the thermal gradient created by the phase-changing solvent has a pressure differential of between about 100 kPa, to about 750 kPa. In some embodiments, the thermal gradient created by the phase-changing solvent has a pressure differential of about 10 kPa, about 20 kPa, about 30 kPa, about 40 kPa, about 50 kPa, about 60 kPa, about 70 kPa, about 80 kPa, about 90 kPa, about 100 kPa, about 110 kPa, about 120 kPa, about 130 kPa, about 140 kPa, about 150 kPa, about 160 kPa, about 170 kPa, about 180 kPa, about 190 kPa, about 200 kPa, about 210 kPa, about 220 kPa, about 230 kPa, about 240 kPa, about 250 kPa, about 260 kPa, about 270 kPa, about 280 kPa, about 290 kPa, about 300 kPa, about 310 kPa, about 320 kPa, about 330 kPa, about 340 kPa, about 350 kPa, about 360 kPa, about 370 kPa, about 380 kPa, about 390 kPa, about 400 kPa, about 410 kPa, about 420 kPa, about 430 kPa, about 440 kPa, about 450 kPa, about 460 kPa, about 470 kPa, about 480 kPa, about 490 kPa, about 500 kPa, about 510 kPa, about 520 kPa, about 530 kPa, about 540 kPa, about 550 kPa, about 560 kPa, about 570 kPa, about 580 kPa, about 590 kPa, about 600 kPa, about 610 kPa, about 620 kPa, about 630 kPa, about 640 kPa, about 650 kPa, about 660 kPa, about 670 kPa, about 680 kPa, about 690 kPa, about 700 kPa, about 710 kPa, about 720 kPa, about 730 kPa, about 740 kPa, about 750 kPa, about 760 kPa, about 770 kPa, about 780 kPa, about 790 kPa, about 800 kPa, about 810 kPa, about 820 kPa, about 830 kPa, about 840 kPa, about 850 kPa, about 860 kPa, about 870 kPa, about 880 kPa, about 890 kPa, about 900 kPa, about 910 kPa, about 920 kPa, about 930 kPa, about 940 kPa, about 950 kPa, about 960 kPa, about 970 kPa, about 980 kPa, about 990 kPa, about 1000 kPa, and values in between, as would be immediately apparent to one of skill. In some embodiments, the thermal gradient created by the phase-changing solvent has a pressure differential less than about 10 kPa, including about 9 kPa, about 8 kPa, about 7 kPa, about 6 kPa, about 5 kPa, about 4 kPa, about 3 kPa, about 2 kPa, about 1 kPa, and values in between, as would be appreciated by one of skill. In some embodiments, the thermal gradient created by the phase-changing solvent has a pressure differential greater than about 1,000 kPa, including about 1,250 kPa, about 1,500 kPa, about 2,000 kPa, about 2,500 kPa, about 3,000 kPa, values in between, as would be apparent to one of skill, and, in some embodiments, above about 3,000 kPa. To create this thermal gradient, and to allow the solvent to enter and exit the necessary phases, energy is applied to the system, both to remove and to add heat. In the embodiments of FIG. 2, this can be accomplished with chiller 207 and heater 208. Thermal gradients as well as temperatures and pressures for different solvents and mixtures thereof will be apparent to those of skill using the teachings herein and general knowledge in the art. Empirical determinations of thermal gradients and pressure differentials will be readily ascertainable by those of ordinary skill, during operation of the invention, and the a priori determination of thermal gradients and pressure differentials that can be used during operation, or that may be optimally used, will also be within ordinary skill, using the teachings herein and the general knowledge in the art.

Chiller 207 can be used to maintain the solvent in a low-energy, liquid state in solvent tank 202. As mentioned, modifiers, such as, but not limited to "low" and "high," are relative terms—meaning a "low energy" solvent merely possesses lower energy than a "high energy" solvent, while a "high energy" solvent merely possesses higher energy than a "low energy" solvent. As its name suggests, chiller 207 keeps the solvent chilled and as a liquid, i.e., at a desired temperature below the boiling point of the solvent at the pressure of the system (as may be calculated by reference to the fundamental gas laws, e.g., the ideal gas law $PV=nRT$ and/or Boyle's law, $P_1V_1=P_2V_2$). The actual temperature is one of the operating parameters that will be chosen depending on the variables sought to be optimized, and is within the knowledge of those of skill. Numerous chilling means are known to those of skill, and include the simple (e.g., cold baths composed of ice water or dry ice pellets in liquid alcohol) as well as more complicated apparatuses (recirculating chillers and other laboratory chillers). As an exemplary embodiment, a recirculating chiller may be used in some embodiments of the invention, wherein the recirculating chiller utilizes a continuous flow of temperature-controlled liquid (which can be specifically set by the operator) with a high pressure, which removes heat from the apparatus to which it is directed.

In some embodiments, the pressure with which the system runs may be calculated through the use of a "temperature and pressure chart," or "P/T Chart." Such charts generally list the refrigerant code (e.g., 22-V, 502-R, 12-F, etc.) in the first cell of each column, beginning with column 2, and a temperature range in the first column arranged in either a descending or ascending order. The rest of the cells within each column headed by a refrigeration code are populated with pressures, each corresponding to the pressure of that refrigerant at a given temperature. Utilizing such charts is routine in the art, and would be understood to those of skill. In some embodiments, the temperature and pressure of the refrigeration circuit is within the parameters for the refrigerant utilized as known in the art.

As would be immediately apparent to one of skill, solvent tank 202 can be chilled continuously, or at specific times during the extraction process, such as when the gaseous solvent is released into the return channel, timed so that it condenses back into a liquid at the chilled temperature as or after it returns to the solvent tank.

For example, maintaining solvent tank 202 at a temperature ranging from about −1.5° C. to about −137.4° C., including about −1.5° C., about −2° C., about −3° C., about −4° C., about −5° C., about −6° C., about −7° C., about −8° C., about −9° C., about −10° C., about −11° C., about −12° C., about −13° C., about −14° C., about −15° C., about −16° C., about −17° C., about −18° C., about −19° C., about −20° C., about −21° C., about −22° C., about −23° C., about −24° C., about −25° C., about −26° C., about −27° C., about −28° C., about −29° C., about −30° C., about −31° C., about −32° C., about −33° C., about −34° C., about −35° C., about −36° C., about −37° C., about −38° C., about −39° C., about −40° C., about −41° C., about −42° C., about −43° C., about −44° C., about −45° C., about −46° C., about −47° C., about −48° C., about −49° C., about −50° C., about −51° C., about −52° C., about −53° C., about −54° C., about −55° C., about −56° C., about −57° C., about −58° C., about −59° C., about −60° C., about −61° C., about −62° C., about −63° C., about −64° C., about −65° C., about −66° C., about −67° C., about −68° C., about −69° C., about −70° C., about −71° C., about −72° C., about −73° C., about −74° C., about −75° C., about −76° C., about −77° C., about −78° C., about −79° C., about −80° C., about −81° C., about −82° C., about −83° C., about −84° C., about −85° C., about −86° C., about −87° C., about −88° C., about −89° C., about −90° C., about −91° C., about −92° C., about −93° C., about −94° C., about −95° C., about −96° C., about −97° C., about −98° C., about −99° C., about −100° C., about −101° C., about −102° C., about −103° C., about −104° C., about −105° C., about −106° C., about −107° C., about −108° C., about −109° C., about −110° C., about −111° C., about −112° C., about −113° C., about −114° C., about −115° C., about −116° C., about −117° C., about −118° C., about −119° C., about −120° C., about −121° C., about −122° C., about −123° C., about −124° C., about −125° C., about −126° C., about −127° C., about −128° C., about −129° C., about −130° C., about −131° C., about −132° C., about −133° C., about −134° C., about −135° C., about −136° C., about −137° C., about −137.4° C., and values in between, as would be apparent to one of skill, is sufficient to maintain the solvent in a liquid phase where the solvent is butane, which has a boiling point of about −1° C., and a melting point of about −138° C. at standard pressure. As would be immediately apparent to one of skill, the temperature required to maintain butane in a liquid phase is also dependent on pressure. Butane remains a liquid at 50° C. or even 100° C. when maintained at pressures of 500 kPa and 1,500 kPa, respectively, while its critical point is reached at about 3,800 kPa and 152° C. Temperatures and pressures for other solvents and mixtures thereof will be readily apparent to those of skill using the teachings herein and the general knowledge in the art. Empirical determinations of temperatures and pressures will be readily ascertainable by those of ordinary skill, during operation of the invention, and the a priori determination of temperatures and pressures that can be used during operation, or that may be optimally used, will also be within ordinary skill, using the teachings herein and general knowledge in the art.

It will be understood that maintaining solvent tank 202 at lower temperatures creates a greater temperature differential between solvent tank 202 and collection tank 204, and the magnitude of that differential drives the heat engine that returns the gaseous solvent and condenses it back into a liquid. More specifically, one of skill will appreciate that the heat engine (or thermal gradient) drives solvent within the extraction system, the end product of which is a "biological compound concentrate," wherein "biological compound concentrate" refers to products extracted from a biological starting material (or "biological material") (NIDA, 2020). In some embodiments, the biological starting material includes cannabis material and, in some embodiments, the biological compound concentrate is a cannabis concentrate. As the invention may be applied in different embodiments to the extraction of compounds from biological materials other than cannabis, such as other plant materials, as well as fungal materials and animal materials, including animal products, animal byproducts, and animal waste, a "biological compound concentrate" may refer to the end product of the processes of the invention, in any such embodiments, using any such biological materials.

Where the invention finds applications in extraction of non-biological materials, such as hydrocarbon extraction in the oil and gas industry, including extraction of hydrocarbon-containing organic matter within coal, oil shale, tar sands and oil sands, crude oil, heavy or extra heavy crude oil, natural gas and petroleum gas, crude bitumen, kerogen, natural asphalt and/or asphaltene, the term "biological compound concentrate" appearing herein may be substituted with the term "non-biological compound concentrate" with modifications to the processes of the invention as would be readily appreciated by those of ordinary skill in view of this disclosure and the general knowledge in the art.

To aid chilling, the solvent can pass from return channel 205 to solvent tank 202 through a condensing coil that is in contact with the chilling means of chiller 207 (e.g., in a cold bath). As it relates to the invention, "in contact with" may refer to "thermal contact," "thermal coupling," "thermally coupled," etc., which refers to two or more bodies sufficiently thermally integrated such that heat may be exchanged between the same. Generally, such thermal integration therefore will be sufficient for purposes of the heat exchange of the embodiment of the invention, within a reasonable degree of efficiency (e.g., heat loss to the environment), as understood to those of skill. "Thermally integrated" as used herein, may refer to any heat transfer between two or more bodies, including but not limited to conduction (or "conductive heat transfer"), wherein heat is transferred from an object of a higher temperature (energy) to that of an object of lower temperature (energy) via direct contact between the atoms of each object; convection, wherein heat is transferred between a surface and a liquid or gas in motion; and radiation, wherein heat is transferred through "empty space," i.e., without an intervening medium (Neese, 2018). Broadly, and without being bound by theory, conductive heat transfer may be illustrated by "Fourier's Law," $q=(k/s)AdT$, wherein "q" is heat transfer, measured as W, J/s, Btu/hr; k is the thermal conductivity of the material, measured as W/m K, W/m ° C., or Btu ft/(h ft 2° F.); s is the material thickness, measured in meters or feet; A is the heat transfer area, measured in $m^2$ or $ft^2$, and dT is $t_1-t_2$, wherein "t" is temperature. In other words, the rate of conductive heat transfer largely depends on the temperature gradient and area of contact between the two bodies, the thickness of each material, and the conductive properties of the two bodies (Sokolova, 2019).

As it relates to thermal contact between the chilling means of the chiller and the condensing coil, "in contact with" will be understood to mean that the chilling means of the chiller is capable of exerting its heat-removing effects on the solvent. In this example, as the gaseous solvent flows through the condensing coil, it recondenses into a liquid phase with greater efficiency because the coil provides increased surface area for thermal energy transfer from the gaseous solvent to chiller 207. In general, one of skill will appreciate that any means of increasing the contact area for thermal energy transfer will increase the energy efficiency of the system. Similarly, other means of increasing the heat transfer coefficient will also result in greater efficiency of the system (e.g., increasing the thermal conductivity through, among other things, utilizing a material with a higher heat transfer coefficient, decreasing the wall thickness of the materials used, and/or optimizing the connection between the chilling means of chiller 207 and the condensing coil, non-limiting examples of which include using welds such as stick welds, mig welds, gas welds, tig welds, and tack welds; thermal pads such as silicone pads, graphite pads, acrylic pads, and aluminum pads; thermal pastes such as zinc oxide, silicone oil, ceramic, aluminum, copper, silver, graphite, and carbon nanoparticles; and soldering (Galvez, 2019), although numerous other forms of integration will be appreciated.

Heater 208 is used to heat the collection tank 204 containing the solvent-extract solution to a temperature at which the solvent enters a gaseous phase (i.e., above its boiling point at the pressure of the system). By heating the collection tank to a temperature that volatilizes the solvent, the solvent transforms to a gaseous phase and separates from the solvent-extract solution leaving the extracted plant compounds behind (at least, in most embodiments, substantially so, and further evaporation will be appreciated as being utilized in some embodiments to remove residual solvent). As collection tank 204 is heated, the gaseous solvent also is drawn through solvent return channel 205 back into solvent tank 202.

Herein, "heating the collection tank," refers to heating the solution in the tank to a temperature above the temperature of the solution prior to entering the tank which, in some embodiments, refers to heating the solution in the tank to a temperature above its boiling point. In other words, reference to heating or chilling a "tank" also refers to heating or chilling the contents of the tank, as would be understood by those of ordinary skill in the art, unless context clearly indicates that reference is specific to the tank itself.

Furthermore, when speaking of "collection tank 204," "collection vessel," "the collection tank," "the collection vessel," "a collection tank," or "a collection vessel," "solvent tank 202," "the solvent tank," or "a solvent tank;" or otherwise generally of "the tank" or "a tank;" one of skill will understand that "tank" generally refers to a vessel constructed of a substantially solid material having a top, a bottom, a means of accessing the interior of the vessel, including but not limited to a "hatch" or a "lid," an interior area, and at least one side operably secured to the top and to the bottom so as to form a sealable container (or form part of a sealable circuit) resistant to leaks and capable of storing (or allowing to pass through) a plurality of substances, those substances including but not limited to solids, such as but not limited to cannabis plant material; liquids, such as but not limited to solvents useful in the process of the invention (e.g., the extraction solvent); and gasses, such as but not limited to those produced as a result of the chemical reactions of the invention. One will also understand that a process or system could utilize one, two, or more than two tanks to serve the same functions (in series or in parallel), and thus any such "tank" will refer to any number of tanks that can be used together in place of a single tank, including where the "tank" is depicted in the Figures. Reference to or depiction of a single "tank" shall be appreciated to be for purposes of describing or illustrating a simple exemplary system, and other systems still within the scope of the invention will, for example, utilize a collection vessel which is separate from an evaporation vessel and which feeds into the evaporation vessel, or multiple such collection vessels and evaporation vessels together.

Thus, for example, "a collection tank" may refer to a separate collection vessel and a separate evaporation vessel. Each may serve a distinct function when separated, for instance, the collection vessel is what first receives the "extraction solution," (a homogenous or heterogenous mixture comprising the cannabis extract and solvent), from the material column and "holds" or "stores" it, from which it feeds into the evaporation vessel, wherein evaporation of the solvent out of the extract takes place. Accordingly, a collection vessel and evaporation vessel may or may not be two (or more) separate apparatuses which may or may not occupy the same chamber. Nonetheless, for simplicity and as a shorthand, and because the functions may be performed together, a "collection tank" herein refers to them together unless otherwise specified.

As with chilling means, numerous heating means also are known to those of ordinary skill, and need not be repeated here. Known methods include warming baths, heat jackets, recirculating heaters, resistive heating elements, thermoelectric heaters, and other heating sources. As with chiller 207, heater 208 can be temperature controlled by a practitioner to achieve a desired temperature, or can heat continuously or at specific times during the extraction process, depending on variables to be optimized. And as with chiller 207, means of increasing the heat transfer coefficient include, but not limited to, utilizing a material with a higher heat transfer coefficient, decreasing the wall thickness of the materials used, and/or optimizing the connection between heater 208 and collection tank 204.

Although in some embodiments of a closed-cycle extraction system there may be other electrical and/or mechanical apparatuses (e.g., one or more pumps) that utilize energy, the primary and most significant demands on energy, and thus significant sources of operating expense, are chiller 207 and heater 208. Reference is now made to FIG. 3, where it will be appreciated how Applicant's invention can provide substantial savings of energy and expense, and will provide numerous measurable and meaningful improvements over the art.

FIG. 3 shows a diagrammatic representation of an exemplary symphasic closed-cycle extraction system, according to one embodiment of the present invention. Keeping the other elements of FIG. 2 together, FIG. 3 demonstrates how chiller 207 and heater 208 are replaced with a closed-cycle refrigeration circuit 300 (herein, "refrigeration circuit").

Closed-cycle refrigeration circuit 300 of FIG. 3 contains four primary components: evaporator 301, compressor 302, condenser 303, and throttling device 304. These components, along with refrigerant line 306 which, in some embodiments, runs between and connects all four of them, creates a sealable, closed loop. Note, refrigerant line 306, in some embodiments, may refer to a single line, or a plurality of lines, as would be apparent to one of skill. Additionally, while refrigerant line 306 appears to continuously run between the various components of closed-cycle refrigeration circuit 300, it should be understood that such is merely for illustrative purposes, and that, in some embodiments, one of skill may conceivably include a variety of components spanning refrigerant line 306, and that such would still be within the spirit of the invention. Non-limiting examples of such devices include gauges, including those measuring temperature and pressure; regulators, sight glasses and view ports, vents, valves, drains, inlets, clamps and connectors, and controllers. Structurally, refrigerant line 306 may be constructed of a substantially solid material (preferably one non-reactive with the contents within) possessing an interior diameter substantial enough to allow the contents within to move freely between the at least two bodies, thereby establishing fluid communication between the same. In some embodiments, refrigerant line 306 is constructed of a substantially flexible material, so that a practitioner is capable of modifying the position of refrigerant line 306 to meet specific needs in a given implementation. In some embodiments, refrigerant line 306 is constructed of a semi-rigid, or substantially rigid material, so as to prevent substantial movement during regular operation. In some embodiments, refrigerant line 306 is sufficiently insulated so as to prevent external conditions from altering the line's internal conditions. In some embodiments, refrigerant line 306 may be constructed of a single substantially-solid material; while in some embodiments, refrigerant line 306 may be constructed of at least two substantially-solid materials, including but not limited to steel, polyvinyl chloride (PVC), and copper. In one embodiment, refrigerant line 306 is constructed of a substantially solid material, such as but not limited to steel, polyvinyl chloride (PVC), and copper; an insulating material surrounding the substantially solid material, such as but not limited to polyurethane foam (or another material having a thermal conductivity of between about 0.024 W/m K to about 0.033 W/m K, including about 0.024 W/m K, about 0.025 W/m K, about 0.026 W/m K, about 0.027 W/m K, about 0.028 W/m K, about 0.029 W/m K, about 0.03 W/m K, about 0.031 W/m K, about 0.032 W/m K, about W/m K, and values in between as would be apparent to one of skill); and an outer casing constructed of a substantially solid material, such as but not limited to high-density polyethylene (HDPE).

Within refrigerant line 306 is refrigerant 305 such as the hydrofluorocarbon (HFC) refrigerants R-134A, R-404A, R-407C, and R-410A, or other refrigerants known in the art to work with refrigeration or heating, ventilation, and air conditioning (HVAC) systems, like refrigerant blends such as R-509A (R-22/218). Exemplary refrigerants also include, but are not limited to, propane (R-290), butane (R-600), and isobutane (R-600A). While those of skill will understand how to select an appropriate refrigerant for use, it will be appreciated that numerous types of refrigerants are available and could be used in the practice of the invention, including such refrigerants as hydrofluorocarbons (HFCs), chlorofluorocarbons (CFCs), hydrochlorofluorocarbons (HCFCs), perfluorocarbons (PFCs), hydrofluoroolefins (HFOs), and hydrocarbons (HCs), as well as those known but not listed here.

In an example cycle depicted in FIG. 3, refrigerant 305 begins as a low-pressure low-temperature gas (at arrow 305) and proceeds clockwise (although the orientation is for diagrammatic purposes only) around refrigerant line 306 to compressor 302. Compressor 302 forces the refrigerant through the system and may be thought of as an "engine" of the refrigeration cycle. As refrigerant 305 passes through compressor 302 it becomes a high-pressure, high-temperature gas. Standard types of HVAC, air conditioning (AC), and refrigeration compressors may be utilized, such as "reciprocating," "scroll," "screw," "rotary," and "centrifugal" compressors. In general, the apparatus and equipment utilized in HVAC, AC, and refrigeration systems can be used for components in the systems of the invention, with the modifications discussed herein or otherwise understood to those of skill.

After compression, refrigerant 305 continues clockwise around refrigerant line 306 to condenser 303. At condenser 303, the high-temperature refrigerant 305 transfers heat to collection tank 204 (or an evaporation vessel, as discussed above). Condenser 303 and collection tank 204 (or, e.g., an evaporation vessel, where separate from a collection vessel) are thermally coupled, as previously discussed, so as to allow efficient heat exchange.

To maximize heat exchange, condenser 303 may be a coil within or surrounding collection tank 204, as such increases surface area available for heat dispersion. Any heat exchanging means may be utilized, such as shell and tube, including "u-tube" or straight-tube heat exchangers, with one or two pass tube sides; or calandria-type systems, or other heat exchangers as would be known to those of skill. In general, one of skill will appreciate that any means of increasing the contact area for thermal energy transfer or increasing the heat transfer coefficient will result in greater efficiency of the system (e.g., increasing thermal conductivity by, among other things, using materials with high thermal conductivities, decreasing the wall thickness of materials used, and/or optimizing the connection between condenser 303 and collection tank 204 (or alternatively, e.g., an evaporation vessel).

As refrigerant 305 passes condenser 303 and transfers heat to collection tank 204, heat is necessarily transferred to the plant extract solution within collection tank 204, which effectuates the goal of vaporizing the solvent therein. Efficient heat exchange with the extract solution thus will be appreciated as an ultimate design goal of how condenser 303 and collection tank 204 are thermally coupled, and means of doing so will be generally understood by one of skill based on the disclosure herein and general knowledge in the art.

As refrigerant 305 passes condenser 303 (and loses heat), the refrigerant changes from a high-pressure, high-temperature gas to a high-pressure, high-temperature liquid. This high-pressure, high-temperature liquid continues clockwise (through refrigerant line 306) and reaches the "control means," illustrated as throttling device 304. Throttling device 304 controls the flow of refrigerant 305, lowering its pressure as it passes through.

After refrigerant 305 leaves throttling device 304, it is now a low-pressure, low-temperature liquid (although, as elsewhere, generally speaking and without being bound by theory, and with empirical determinations during actual operation capable of being made by operators of ordinary skill in the art). Throttling device 304 can be any throttling device known to those of skill to be useful as a component in refrigeration and air conditioning systems to control the amount of refrigerant released into the evaporator and to regulate the heat of the vapor leaving the evaporator.

Herein, "control means" refers to any device capable of controlling the flow of a fluid, wherein "fluid" broadly refers to its common definition, i.e. a substance having no fixed shape that yields to external pressure. In some embodiments, the control means is capable of dissipating pressure energy by irreversibly converting the pressure energy into thermal energy. In some embodiments, the "control means" is a throttling device.

In some embodiments, "throttling device," "throttling valve," "expansion valve" and the like, including those useful in the invention, refer to valves that control the flow of a fluid in a closed-loop refrigeration circuit. In some embodiments, the throttling device is a device capable of irreversibly converting pressure energy to thermal energy. In some embodiments, the conversion of pressure energy to thermal energy is completed through dissipative viscous flow processes, as would be appreciated by one of skill. In some embodiments, the throttling device has the same, or substantially the same inlet and outlet flow velocities; while in some embodiments, the throttling device has an inlet pressure higher than the outlet pressure. In some embodiments, the pressure differential between the inlet pressure and the outlet pressure is between about 1 kPa to about 1,000 kPa. In some embodiments, the pressure differential between the inlet pressure and the outlet pressure is about 10 kPa, about 20 kPa, about 30 kPa, about 40 kPa, about 50 kPa, about 60 kPa, about 70 kPa, about 80 kPa, about 90 kPa, about 100 kPa, about 110 kPa, about 120 kPa, about 130 kPa, about 140 kPa, about 150 kPa, about 160 kPa, about 170 kPa, about 180 kPa, about 190 kPa, about 200 kPa, about 210 kPa, about 220 kPa, about 230 kPa, about 240 kPa, about 250 kPa, about 260 kPa, about 270 kPa, about 280 kPa, about 290 kPa, about 300 kPa, about 310 kPa, about 320 kPa, about 330 kPa, about 340 kPa, about 350 kPa, about 360 kPa, about 370 kPa, about 380 kPa, about 390 kPa, about 400 kPa, about 410 kPa, about 420 kPa, about 430 kPa, about 440 kPa, about 450 kPa, about 460 kPa, about 470 kPa, about 480 kPa, about 490 kPa, about 500 kPa, about 510 kPa, about 520 kPa, about 530 kPa, about 540 kPa, about 550 kPa, about 560 kPa, about 570 kPa, about 580 kPa, about 590 kPa, about 600 kPa, about 610 kPa, about 620 kPa, about 630 kPa, about 640 kPa, about 650 kPa, about 660 kPa, about 670 kPa, about 680 kPa, about 690 kPa, about 700 kPa, about 710 kPa, about 720 kPa, about 730 kPa, about 740 kPa, about 750 kPa, about 760 kPa, about 770 kPa, about 780 kPa, about 790 kPa, about 800 kPa, about 810 kPa, about 820 kPa, about 830 kPa, about 840 kPa, about 850 kPa, about 860 kPa, about 870 kPa, about 880 kPa, about 890 kPa, about 900 kPa, about 910 kPa, about 920 kPa, about 930 kPa, about 940 kPa, about 950 kPa, about 960 kPa, about 970 kPa, about 980 kPa, about 990 kPa, about 1000 kPa, and values in between, as would be immediately apparent to one of skill. In some embodiments, the pressure differential between the inlet pressure and the outlet pressure is less than about 10 kPa, including about 9 kPa, about 8 kPa, about 7 kPa, about 6 kPa, about 5 kPa, about 4 kPa, about 3 kPa, about 2 kPa, about 1 kPa, and values in between, as would be appreciated by one of skill. In some embodiments, the pressure differential between the inlet and the outlet pressure is greater than about 1,000 kPa, including about 1,250 kPa, about 1,500 kPa, about 2,000 kPa, about 2,500 kPa, about 3,000 kPa, and values in between, as would be appreciated by one of skill. Pressure differentials as well as temperatures and pressures for different solvents and mixtures thereof will be readily apparent to those of skill using the teachings herein and the general knowledge in the art. Empirical determinations of pressure differentials will be readily ascertainable by those of ordinary skill, during operation of the invention, and the a priori determination of pressure differentials that can be used during operation, or that may be optimally used, will also be within ordinary skill, using the teachings herein and the general knowledge in the art.

In some embodiments, the throttling device will cause a change in cross-sectional area. In some embodiments, the change in cross-sectional area includes a reduction in area, followed by an increase in area. In some embodiments, wherein the change in cross-sectional area includes a reduction in area, the reduction in area is between about 1 mm to about 20 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, and values in between, as would be apparent to one of skill. In some embodiments, the change in cross-sectional area is a reduction in cross-section area of less than about 1 mm, including about 0.9 mm, about 0.8 mm, about 0.7 mm, about 0.6 mm, about 0.5 mm, about 0.4 mm, about 0.3 mm, about 0.2 mm, about 0.1 mm, about 0.01 mm, about 0.001 mm, and values in between, as would be apparent to one of skill. In some embodiments, the change in cross-sectional area is a reduction in cross-sectional area of more than about 20 mm, including about 25 mm, about 30 mm, about 40 mm, about 50 mm, about 75 mm, about 100 mm, about 150 mm, about 250 mm, and values in between, as would be apparent to one of skill. Empirical determinations of the change in cross-sectional area will be readily ascertainable by those of ordinary skill, during operation of the invention, and the a priori determination of the change in cross-sectional areas that can be used during operation, or that may be optimally used, will also be within ordinary skill, using the teachings herein and the general knowledge in the art.

In some embodiments, wherein the change in cross-sectional area is an increase in cross-sectional area, the increase in area is between about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, and values in between, as would be apparent to one of skill. In some embodiments, the change in cross-sectional area is an increase in cross-section area of less than about 1 mm, including about 0.9 mm, about 0.8 mm, about 0.7 mm, about 0.6 mm, about 0.5 mm, about 0.4 mm, about 0.3 mm, about 0.2 mm, about 0.1 mm, about 0.01 mm, about 0.001 mm, and values in between, as would be apparent to one of skill. In some embodiments, the change in cross-sectional area is an increase in cross-sectional area of more than about 20 mm, including about 25 mm, about 30 mm, about 40 mm, about 50 mm, about 75 mm, about 100 mm, about 150 mm, about 250 mm, and values in between, as would be apparent to one of skill.

In some embodiments, the degree to which the fluid contracts in the section having a reduced area is calculable via Bernoulli's equation (Tan and Dong, 2021). In some embodiments, the throttling device possesses an internal velocity and pressure gradient that results in a permanent loss in pressure ($\Delta P$) from the inlet pipe to the outlet pipe connections (Cashco, n.d.).

In some embodiments, a throttling device refers to a structure placed between a condenser and an evaporator in a closed refrigeration cycle useful in depressurizing a refrigerant between a first chamber connected to the condenser and a second chamber connected to the evaporator, wherein the refrigerant moves from the condenser, through the throttling device, to the evaporator. In some embodiments, a throttling device is insulated such that external conditions do not affect the internal conditions of the throttling device.

In some embodiments, "throttling device" refers to valves in which the opening degree is varied corresponding to a differential pressure between a fluid. In some embodiments, the throttling device may include a porous plug, an orifice plate, a butterfly valve, any type of flow or pressure control valve, or may simply employ geometry that causes a sudden contraction (reduction in area), a sudden expansion (increase in area), or a combination thereof (such as a contraction followed by an expansion, or an expansion followed by a contraction), so long as the desired effect of a reduction in pressure from the inlet flow to the outlet flow is realized.

Examples of throttling devices will be understood to include expansion valves and other fluid control means, such as valves or tubing that control the flow of refrigerant through an opening or "orifice" so that the pressure of refrigerant drops as the refrigerant passes through the throttling device, or other fluid control means, and expands. Those of skill will appreciate this rapid change in pressure as a significant driver of the system's circulation, and will recognize "control means," or "fluid control means" as including such throttling devices as capillary tube valves, constant pressure or automatic throttling valves, thermostatic expansion valves (i.e., TEVs, TXVs, or TX valves), float valves, electronic expansion valves, throttling pipes, "metering devices," and the like.

In some embodiments, the throttling device is a thermostatic expansion valve (TXV), such as those commonly used in refrigerator and air conditioning systems. TXVs effectively control the amount of refrigerant liquid injected into the system's evaporator, based on the evaporator outlet temperature and pressure (Danfoss, 2017). While there are many different types of TXVs, they will generally contain a diaphragm, a power element, a setting spring, and an orifice (Danfoss, 2017). Functionally, but without being bound by theory, there are three forces at work in a TXV that determine whether the valve will open or close: bulb pressure, spring pressure, and evaporator pressure, the first of which originates from the bulb mounted at the outlet of the evaporator, which senses the suction temperature and drives the diaphragm down in response to an increase. Spring pressure, in contrast, constantly pushes up against the diaphragm—necessarily counter to the bulb pressure (the specific pressure the spring exerts on the diaphragm is manually calibrated prior to installation). Lastly, evaporator pressure pushes the diaphragm up when the suction pressure increases due to evaporator load on the system (which varies according to different operating conditions, including but not limited to temperature changes) (Danfoss, 2017).

In some embodiments, the throttling device is a capillary tube. Capillary tubes generally include a long, coiled tube of a substantially small internal diameter (usually between about 0.5 mm to about 2.3 mm), constructed of a substantially solid material, such as but not limited to copper, that directly connects a condenser to an evaporator (Bright Hub Engineering, 2009). As would be appreciated by one of skill, the specific loss in pressure from the capillary tube's inlet to its outlet is determined not by an orifice, but by the length of the tube and its diameter—with a decrease in pressure corresponding to a decrease in internal diameter and increase in length (id.). Unlike TXV implementations, the fluid flow control is fixed, so it is important the length and internal diameter are selected for the specific implementation in which the capillary tube will be deployed (Ashlin, 2020). While relatively simple implementations, capillary tubes do offer a few unique advantages, including but not limited to the low price of the components and the lack of maintenance needed to maintain the system. In embodiments when refrigerant is substantially viscous, it may be advantageous to have a screen or strainer on the exterior of the inlet valve to prevent clogging.

In some embodiments, the throttling valve is an automatic control valve, wherein the flow is controlled via signals generated by independent devices such as, but not limited to, flow meters or temperature gauges (Flomatic Valves, 2021). As would be appreciated by one of skill, automatic control valves are generally fitted with actuators and positioners. In some embodiments, actuators may be pneumatically-actuated, such as pneumatically-actuated globe valves. In some embodiments, quarter-turn valves such as modified ball and butterfly valves may be utilized (Flomatic Valves, 2021). In some embodiments, hydraulic actuators (also known as hydraulic pilots) may be utilized. Functionally, like other throttling valves, automatic control valves regulate the flow of a fluid by opening, closing, or partially obstructing their various passageways.

In some embodiments, the throttling valve is a float valve. Broadly, a float valve is a simple mechanical liquid level controller that detects changes of elevation in the liquid's free surface and opens or closes a valve accordingly (Nesbit, 2007). Float valves are common in various types of domestic water systems, including but not limited to toilets and water heaters, wherein the float valve regulates the flow and level of water in such systems, e.g., the volume of flush water. Float valves are generally constructed of brass, bronze, injection-molded plastic, cast iron, and/or stainless steel (Nesbit, 2007). As would be appreciated by one of skill, high operating torque can be solved through the utilization of a "balanced" float valve, wherein the float valve is comprised of a single valve and a balanced piston, the latter having the same area as the valve, but is loaded in the opposite direction (Nesbit, 2007). As mentioned, this significantly reduces the operating torque, but does introduce nominal friction by the balance piston seal. However, as would be appreciated by one of skill, this friction can be beneficial in dampening modulation induced by "waves" that may form on the surface of the liquid.

In some embodiments, the throttling device of the invention may be an electronic expansion valve. Structurally, electronic expansion valves (EEVs) include a motor and driver assembly, a locknut, a main body, an outlet, a port, a pin, a strainer, and an inlet (Tomczyk, 2019). Functionally, EEVs control the flow of refrigerant entering a direct expansion evaporator, doing so in response to signals sent by an electronic controller. Generally, a small motor (called a "step" or "stepper" motor is utilized to open and close the valve port, the motor only rotating (a fraction of a revolution, called a "step") for each signal received from the electronic controller (Tomczyk, 2019). The step motor itself is powered by a gear train, which positions a pin in a port in which refrigerant flows. Step motors can run at 200 "steps" per second, and are capable of rapidly returning to their exact position (Tomczyk, 2019). Most EEVs have over 1,500 steps of control, each being around 1.9 µm. Regarding the signals themselves, most are sent by a "thermistor" which is a resistor that changes its resistance as it experiences temperature changes (Tomczyk, 2019). Other sensors may also be located at the evaporator inlet and outlet, which protect the compressor from any liquid floodback under low "superheat" conditions, wherein superheat refers to the difference between the actual temperature of the refrigerant vapor at a given point and the saturation temperature of the refrigerant (Tomczyk, 2019). In some embodiments, pressure transducers can also be wired to the controller for pressure/temperature and superheat control. Structurally, pressure transducers generally have three wires, two of which supply power, and the last serving as an output signal. The controller uses this voltage to calculate the temperature of the refrigerant with the use of a pressure/temperature table programmed into the controller (Tomczyk, 2019).

Broadly, one of skill will understand how to prevent, avoid, and diminish problems that may result from the use of throttling devices, such as cavitation. Herein, "cavitation" refers to a build-up of air bubbles within the compressed liquid flowing into the throttling device, wherein the presence of such air bubbles greatly reduces the available area for the compressed liquid (bubbles require nearly 200-800 times as much volume as a comparable liquid mass) thereby increasing the average fluid velocity (Cashco, n.d.). Cavitation may also lead to a spontaneous "implosion," wherein the vapor bubbles suddenly collapse. If this occurs in the body of the fluid, vibration is the only consequence. However, if present along the walls of the tubing, fatigue and structural damage over time may be observed—reducing the lifespan of the system (Cashco, n.d.). As cavitation is caused by internal fluid pressure conditions, and not flow rate, it is paramount that—if the system is prone to cavitation—the reduction in pressure is completed in stages, rather than all at once. As would be appreciated by one of skill, this may be completed by utilizing a globe or eccentric plug throttling valve rather than a ball or butterfly throttling valve (Cashco, n.d.).

The low-pressure low-temperature liquid refrigerant 305 that leaves throttling device 304 continues clockwise via refrigerant line 306 until it reaches evaporator 301. At evaporator 301, solvent tank 202 transfers heat to the low-temperature refrigerant 305. Evaporator 301 and solvent tank 202 are thermally coupled so as to allow efficient heat exchange. For example, evaporator 301 may be a coil within or surrounding solvent tank 202 to maximize surface area, a shell and tube or calandria-type system, or another appropriate heat exchanging means, as previously discussed. In general, one of skill will appreciate that any means of increasing the contact area for thermal energy transfer or increasing the heat transfer coefficient will result in greater efficiency of the system (e.g., increasing thermal conductivity, decreasing wall thickness of materials used, etc.). The principles here are similar to those discussed with regard to the thermal coupling between condenser 303 and collection tank 204.

As refrigerant 305 passes evaporator 301 and receives heat from solvent tank 202, heat is also received from the solvent within solvent tank 202, which effectuates the goal of condensing the solvent therein. Efficient heat exchange with the solvent thus will be appreciated as an ultimate design goal of how evaporator 301 and solvent tank 202 are thermally coupled, and means of so doing will be generally understood in light of the description herein.

As refrigerant 305 passes evaporator 301 (and absorbs heat), the refrigerant changes (speaking broadly and generally, as will be readily appreciated, with empirical determinations capable of being made by skilled artisans) from a low-pressure, low-temperature liquid to a low-pressure, low-temperature gas. This low-pressure, low-temperature gas continues clockwise via refrigerant line 306 until it reaches compressor 302, restarting the cycle.

At each stage, reference to temperature, pressure, and phase is intended to be suggestive rather than precise; for example, refrigerant leaving a throttling device in fact may be a low-pressure low-temperature mix of liquid and gas. Additionally, reference is relative rather than absolute; a "low temperature" gas is lower temperature than a "high temperature" gas, but reference to a "low temperature gas" and a "low temperature liquid" should not be understood to indicate an equal or similar temperature between the gas and the liquid.

Additionally, while the refrigerant has been referenced as moving "clockwise," such is only for illustrative purposes, as previously discussed. As would be immediately apparent to one of skill, the system could certainly be constructed in a manner in which the refrigerant flows "counter-" or "anti-" clockwise, or, in some embodiments, wherein the refrigerant flows both clockwise and counterclockwise, and where either way is only one of perspective.

Further illustrating the steps of the exemplary process just described, FIG. 4 is a diagrammatic representation of a closed-cycle refrigeration circuit according to an embodiment of the symphasic closed-cycle extraction system. FIG. 4 shows an exemplary refrigeration circuit used in the practice of the invention, as in FIG. 3, and in particular 300, and as in a closed-cycle heat exchange device as described and claimed. FIG. 4 highlights, figuratively, the exchange of heat between the refrigeration circuit and certain components of the solvent extraction circuit (and expresses graphically in each quadrant the resultant typical pressures and phases of matter)—but, for simplicity's sake, does not show all components of the solvent extraction circuit, such as the material column and return channel, and the connections between the components, etc., as will be readily appreciated to those of skill.

As in the example cycle described above, refrigerant 305 begins as a low-pressure, low-temperature gas (at arrow 305) and proceeds clockwise via refrigerant line 306 to compressor 302. Quadrant 401 indicates that during this stage of the cycle, refrigerant 305 is (generally and relatively speaking, here and elsewhere) a low-pressure, low-temperature gas.

After passing through compressor 302 and into quadrant 402, refrigerant 305 is a high-pressure, high-temperature gas. Refrigerant 305 then passes through condenser 303 where it transfers heat—represented by the symbol Q—to collection tank 204, and more importantly the solvent-extract solution therein (causing the solvent to vaporize to a gas).

After passing through condenser 303 and losing heat, refrigerant 305 enters quadrant 403 where it is a high-pressure high-temperature liquid. Refrigerant 305 then passes through throttling device 304 and enters quadrant 404 as a low-pressure low-temperature liquid.

Refrigerant 305 then passes through evaporator 301 where it absorbs heat—again represented by the symbol Q—from solvent tank 202, and more importantly from the solvent therein, (causing the solvent to condense to a liquid).

After passing through evaporator 301 and absorbing heat, refrigerant 305 returns to quadrant 401 as a low-pressure low-temperature gas (again, as elsewhere, only generally and relatively speaking).

From quadrant 401, the refrigeration cycle will continue. Of course, it will be readily appreciated that refrigerant 305 is not "in" any one quadrant, but rather constantly passing through the entirety of refrigerant line 306 as the process runs; hence, conceiving of refrigerant moving through the line as such is simply for ease of figuratively and conceptually explaining the various stages of the process (as is conceiving of the process in "quadrants").

Structurally, metal (or substantially metal) components such as the solvent tank 202, material column 203, and collection tank 204 can be constructed of food grade stainless steel or other suitable medical or food grade materials, preferably those that are non-reactive with the chosen solvent and those having a high thermal conductivity. Note, as it relates to the invention, the qualifier "high" refers to, in this case, a material having a thermal conductivity higher than a material possessing a "low" thermal conductivity, as would be appreciated by one of skill. In some embodiments, a "high" thermal conductivity material, measured as (W/m K), wherein "W" is Watts, "m" is meters, and "K" is kelvin, has a thermal conductivity (k) of at least about 10 W/m K, at least about 20 W/m K, at least about 30 W/m K, at least about 40 W/m K, at least about 50 W/m K, at least about 60 W/m K, at least about 70 W/m K, at least about 80 W/m K, at least about 90 W/m K, at least about 100 W/m K, at least about 110 W/m K, at least about 120 W/m K, at least about 130 W/m K, at least about 140 W/m K, at least about 150 W/m K, at least about 160 W/m K, at least about 170 W/m K, at least about 180 W/m K, at least about 190 W/m K, at least about 200 W/m K, at least about 210 W/m K, at least about 220 W/m K, at least about 230 W/m K, at least about 240 W/m K, at least about 250 W/m K, at least about 260 W/m K, at least about 270 W/m K, at least about 280 W/m K, at least about 290 W/m K, at least about 300 W/m K, at least about 310 W/m K, at least about 320 W/m K, at least about 330 W/m K, at least about 340 W/m K, at least about 350 W/m K, at least about 360 W/m K, at least about 370 W/m K, at least about 380 W/m K, at least about 390 W/m K, at least about 400 W/m K, at least about 410 W/m K, at least about 420 W/m K, at least about 430 W/m K, at least about 440 W/m K, at least about 450 W/m K, at least about 460 W/m K, at least about 470 W/m K, at least about 480 W/m K, at least about 490 W/m K, or at least about 500 W/m K. In some embodiments, the thermal conductivity of the material utilized in the invention is greater than about 500 W/m K, such as at least about about 550 W/m K, at least about about 575 W/m K, at least about about 600 W/m K, at least about about 650 W/m K, or at least about about 700 W/m K.

As would be appreciated by one of skill, connecting lines such as solvent return channel 205 can be constructed of a flexible, semi-rigid, or rigid connection, such as a hose, flexible piping, high pressure flexible line, or other suitable connection known to those of ordinary skill. In some embodiments, the connecting lines are constructed of an insulating material (or are surrounded by an insulating material) so as to preserve the internal conditions within the line. Exemplary embodiments include, but are not limited to, pipes constructed of a substantially solid material, such as but not limited to steel, polyvinyl chloride (PVC), and copper; an insulating material, such as but not limited to polyurethane foam (or another material having a thermal conductivity of between about 0.024 W/m K to about 0.033 W/m K, including about 0.024 W/m K, about 0.025 W/m K, about 0.026 W/m K, about 0.027 W/m K, about 0.028 W/m K, about 0.029 W/m K, about 0.030 W/m K, about 0.031 W/m K, about 0.032 W/m K, about 0.033 W/m K, and values in between, as would be apparent to one of skill) surrounding the aforementioned pipe; and an outer casing constructed of a substantially solid material such as, but not limited to, high-density polyethylene (HDPE) (Logstor, 2011). That said, as mentioned, such an embodiment is purely exemplary in nature, and the piping material, insulating material, and outer casing may be constructed of any materials capable of providing protection for the contents housed within while preserving the internal conditions of the pipe (i.e., preventing heat loss to the surrounding environment, or gaining heat from the surrounding environment, when such is not desired). In addition, connecting means, such as threaded connections, bolted clamps, and releasable connections, such as compression clamps and pin-hinged clamps all may be used, and such may be with or without filters, and with or without gaskets such as nitrile (e.g., buna-N) gaskets, as would be understood by those of skill. Note, as would be appreciated by one of skill, the connecting lines, solvent tank, material column, collection tank, and connecting means may all be made of the same, different, or a combination of the same or different materials, depending on the variables sought to be optimized.

While the methods described and illustrated herein may include particular steps, it should be apparent that other methods including fewer, more, or different steps than those described and shown are also within the spirit and scope of the present invention. The methods and uses of the device and associated steps shown herein therefore should be understood as being provided for purposes of illustration, not limitation. It should be further understood that the specific order or hierarchy of steps in the methods and uses of the device disclosed are only exemplary approaches. Based upon operator and design preferences, the specific order or hierarchy of steps in the methods and uses of the device may be rearranged while remaining within the spirit and scope of the present disclosure. The accompanying claims present elements of the steps in a sample order, and are not meant to be limited to the specific order presented.

Unless otherwise stated, all measurements, values, ratings, positions, magnitudes, sizes, locations, orientations, configurations, and other specifications that are set forth (either expressly or impliedly) in this specification, including in the figures and in the claims that follow, are approximate, and not exact. They are intended to have a reasonable range that is consistent with the functions to which they relate and with what is customary in the art to which they pertain.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise forms disclosed; of course, many modifications and variations are possible in view of the above teachings. The embodiments were chosen and described in order to best explain certain key principles of the invention and its practical applications, through the elucidation of specific examples, and to thereby enable others skilled in the art to best make and utilize the invention and various embodiments with various modifications as are suited to the particular use contemplated, even when such uses are beyond the specific examples disclosed. Accordingly, the scope of the invention shall be defined solely by the following claims and their equivalents.

REFERENCES

1. *Alcohol extraction*. Leafly. (2021, February 4). Retrieved Dec. 3, 2021, from https://www.leafly.com/learn/cannabis-glossary/alcohol-extraction.
2. Angstrom-Tech-Admin (Apr. 20, 2016). "What's the Difference Between Positive and Negative Air Pressure Cleanrooms?". Angstrom Technology.
3. *Automatic Control Valve Products. Flomatic Valves.* (2021, July 21). Retrieved Nov. 26, 2021, from https://www.flomatic.com/valves/automatic-control-valves/.
4. Ashlin. (2020, June 15). *What is a capillary tube and why do we need it*. Instrumentation and Control Engineering. Retrieved Nov. 26, 2021, from https://automationforum.co/what-is-a-capillary-tube-and-why-do-we-need-it/.
5. Bennett, P. (2021, July 8). *What is hash?* Leafly. Retrieved Nov. 14, 2021, from https://www.leafly.com/learn/consume/dabs/what-is-hashish.
6. Bright Hub Engineering. (2009, December 4). *Capillary tube refrigeration. Capillary tube in refrigeration, Air Conditioning*. Bright Hub Engineering. Retrieved Dec. 7, 2021, from https://www.brighthubengineering.com/hvac/58420-capillary-tube-for-refrigeration-and-air-conditioning-systems/.
7. *Butane—thermophysical properties*. Engineering ToolBox. (2008). Retrieved Dec. 10, 2021, from https://www.engineeringtoolbox.com/butane-d_1415.html.
8. *Butane extraction: Using blended solvents for the best bho*. Professional Extraction Equipment. (2016, October 16). Retrieved Nov. 14, 2021, from https://precisionextraction.com/2016/10/blended-solvents-butane-propane-extraction/.
9. BVV. (2018, October 24). *The role of butane/propane in plant extraction*. BVV. Retrieved Nov. 14, 2021, from https://shopbvv.com/blogs/bvv-resources/the-role-of-butane-propane-in-plant-extraction.
10. Cashco. (n.d.). Fluid flow basics of throttling valves. Retrieved Nov. 23, 2021, from https://www.controlglobal.com/assets/Media/MediaManager/RefBook-_Cashco_Fluid.pdf
11. Cunha, V M., Silva, M. P., Costa, W. A., Oliveira, M. S., Bezerra, F. W., Melo, A. C., Pinto, R. H., Machado, N. T., Araujo, M. E., & Junior, R. N. (2018). Carbon dioxide use in high-pressure extraction processes. *Carbon Dioxide Chemistry, Capture and Oil Recovery*. https://doi.org/10.5772/intechopen.71151
12. Engineering ToolBox, (2003). Conductive Heat Transfer. [online] Available at: https://www.engineeringtoolbox.com/conductive-heat-transfer-d 428.html
13. Fan et al. (Nov. 11, 2015). U.S. Pat. No. 9,181,468 "Extraction of hydrocarbons from hydrocarbon-containing materials and/or processing of hydrocarbon-containing materials"
14. Galvez, C. (2019, November 22). *Thermal Compound Buying Guide*. Newegg. Retrieved Dec. 7, 2021, from https://www.newegg.com/insider/thermal-compound-buying-guide/.
15. Hemp production. Hemp Production|Agricultural Marketing Service. (2018). Retrieved Dec. 7, 2021, from https://www.ams.usda.gov/rules-regulations/hemp.
16. How thermostatic expansion valves work. Danfoss. (2017, December 15). Retrieved Nov. 26, 2021, from https://www.danfoss.com/en-us/service-and-support/case-stories/dcs/how-thermostatic-expansion-valves-work/.
17. *Industrial hemp*. Department of Agriculture. (2021). Retrieved Dec. 9, 2021, from https://ag.colorado.gov/plants/industrial-hemp.
18. June-Wells, M. (2020, February 11). *Your guide to ethanol extraction in cannabis. Cannabis Business Times. Retrieved Nov.* 12, 2021, from https://www.cannabisbusinesstimes.com/article/your-guide-to-ethanol-extraction/.
19. Kraft, F. (2013). *Otto von Guerickes neue (sogenannte) Magdeburger Versuche Uber den leeren raum*. Springer.
20. Krawcke, N. (2019, April 17). *A beginning HVAC Tech's Guide for Understanding Superheat*. ACHR News RS S. Retrieved Nov. 26, 2021, from https://www.achrnews.com/articles/141034-a-beginning-hvac-techs-guide-for-understanding-superheat.
21. Logstor. (2011). *The bonded pipe system overview.*
22. Neese, B. (2018, March 13). *Three types of heat transfers*. Sciencing. Retrieved Dec. 10, 2021, from https://sciencing.com/three-types-heat-transfers-5422262.html.
23. Nesbitt, B. (2007). *Handbook of valves and actuators*. Elsevier in association with Roles & Associates Ltd.
24. NIDA. 2020, June 25. *Marijuana Concentrates DrugFacts*. Retrieved from https://www.drugabuse.gov/publications/drugfacts/marijuana-concentrates on 2021, December 7
25. Orge, F. (Jul. 8, 2014). U.S. Pub. No. 2013/0165840A1. "Fluid communication device and method of use thereof"
26. *Recirculating Chiller F-305/F-308/F-314*. Recirculating Chiller F-305/F-308/F-3141 Buchi.com. (2021). Retrieved Dec. 7, 2021.
27. Russo, Taming THC: potential cannabis synergy and phytocannabinoid-terpenoid entourage effects, British J. of Pharm., 163:1344-64 (2011).)
28. Sokolova, I. (2019). Temperature Regulation. In *Encyclopedia of ecology* (2nd, pp. 633-639). essay, Elsevier.
29. Stengel, J. (2019, November 1). *Understanding Supercritical Carbon Dioxide (CO2) extraction*. Cole. Retrieved Nov. 12, 2021, from https://www.coleparmer.com/tech-article/supercritical-co2-extraction-method.
30. Takada et al. (Jul. 19, 2018). U.S. Pat. No. 10,208,867. "Throttling device and refrigeration cycle"
31. Tan, C., & Dong, F. (2021). Sensor instrumentation for flow measurement. *Reference Module in Biomedical Sciences.* https://doi.org/10.1016/b978-0-12-822548-6.00074-1
32. Tomczyk, J. (2019, July 25). *Electronic expansion valves: The basics*. ACHR News RSS. Retrieved Nov. 26, 2021, from https://www.achrnews.com/articles/95056-electronic-expansion-valves-the-basics

The invention claimed is:

1. A system for extraction of compounds from biological material, the system comprising:
   (a) a closed-cycle solvent extraction circuit comprising:
      (i) a solvent tank, structured to hold an extraction solvent;
      (ii) a material column, structured to hold a biological material for extraction;
      (iii) a collection tank, structured to receive the extraction solution; and
      (iv) a return channel, structured to provide fluid communication between the collection tank and the solvent tank; and
   (b) a closed-cycle refrigeration circuit comprising:
      (i) an evaporator, thermally coupled to the solvent tank;
      (ii) a compressor;

(iii) a condenser, thermally coupled to the collection tank; and
(iv) a throttling device or a control means for controlling a flow of a refrigerant between the condenser and the evaporator.

2. The system of claim 1, wherein the refrigeration circuit is capable of creating a thermal gradient to drive solvent within the extraction circuit.

3. The system of claim 2, wherein the thermal gradient to drive solvent is created by a transfer of heat from the condenser to the collection tank and a transfer of heat from the solvent tank to the evaporator.

4. The system of claim 2, wherein the thermal gradient drives solvent within the extraction circuit, so that a biological compound concentrate is obtained from the biological material.

5. The system of claim 4, wherein the biological material is a plant material and the solvent is effective for the extraction of a plant compound concentrate from the plant material.

6. The system of claim 4, wherein the biological material is a *cannabis* material and the solvent is effective for the extraction of a *cannabis* concentrate comprising one or more cannabinoids, and optionally one or more terpenes, from the *cannabis* material.

7. The system of claim 4, wherein the solvent is propane, butane, isobutane, pentane, isopentane, hexane, petroleum ether, methyl tert-butyl ether, diethyl ether, ethanol, methanol, or any mixture thereof.

8. A system for extraction of compounds from biological material, the system comprising:
(a) a closed-cycle solvent extraction circuit comprising:
   (i) a solvent tank, structured to hold an extraction solvent;
   (ii) a material column, structured to hold a biological material for extraction;
   (iii) a collection vessel, structured to receive the extraction solution;
   (iv) an evaporation vessel, fluidly coupled to the collection vessel; and
   (v) a return channel, structured to provide fluid communication between the evaporation vessel and the solvent tank; and
(b) a closed-cycle refrigeration circuit comprising:
   (i) an evaporator, thermally coupled to the solvent tank;
   (ii) a compressor;
   (iii) a condenser, thermally coupled to the evaporation vessel; and
   (iv) a throttling device or a control means for controlling a flow of a refrigerant between the condenser and the evaporator.

9. The system of claim 8, wherein the refrigeration circuit is capable of creating a thermal gradient to drive solvent within the extraction circuit.

10. The system of claim 9, wherein the thermal gradient to drive solvent is created by a transfer of heat from the condenser to the evaporation vessel and a transfer of heat from the solvent tank to the evaporator.

11. The system of claim 9, wherein the thermal gradient drives solvent within the extraction circuit, so that a biological compound concentrate is obtained from the biological material.

12. The system of claim 11, wherein the biological material is a plant material and the solvent is effective for the extraction of a plant compound concentrate from the plant material.

13. The system of claim 11, wherein the biological material is a *cannabis* material and the solvent is effective for the extraction of a *cannabis* concentrate comprising one or more cannabinoids, and optionally one or more terpenes, from the *cannabis* material.

14. The system of claim 11, wherein the solvent is propane, butane, isobutane, pentane, isopentane, hexane, petroleum ether, methyl tert-butyl ether, diethyl ether, ethanol, methanol, or any mixture thereof.

15. A closed-cycle heat exchange device thermally coupled to a solvent extraction system for extraction of compounds from biological material, the device comprising:
(a) an evaporator;
(b) a compressor;
(c) a condenser; and
(d) a throttling device or a control means for controlling the flow of a refrigerant between the condenser and the evaporator;
wherein the evaporator is thermally coupled to a solvent tank of the solvent extraction system, and the condenser is thermally coupled to a collection tank or an evaporation vessel of the solvent extraction system; and
wherein the device is capable of creating a thermal gradient to drive a solvent in the solvent extraction system.

16. The closed-cycle heat exchange device of claim 15, wherein the thermal gradient to drive solvent is created by a transfer of heat from the condenser to the collection tank or the evaporator vessel, and a transfer of heat from the solvent tank to the evaporator.

17. The closed-cycle heat exchange device of claim 15, wherein the thermal gradient drives solvent within the solvent extraction system, so that a biological compound concentrate is obtained from the biological material.

18. The closed-cycle heat exchange device of claim 17, wherein the biological material is a plant material and the solvent is effective for the extraction of a plant compound concentrate from the plant material.

19. The closed-cycle heat exchange device of claim 17, wherein the biological material is a *cannabis* material and the solvent is effective for the extraction of a *cannabis* concentrate comprising one or more cannabinoids, and optionally one or more terpenes, from the *cannabis* material.

20. The closed-cycle heat exchange device of claim 17, wherein the solvent is propane, butane, isobutane, pentane, isopentane, hexane, petroleum ether, methyl tert-butyl ether, diethyl ether, ethanol, methanol, or any mixture thereof.

* * * * *